United States Patent

Fujita et al.

[11] Patent Number: 6,028,193
[45] Date of Patent: Feb. 22, 2000

[54] METHOD FOR PRODUCING ARYL AKLYL HYDROPEROXIDES

[75] Inventors: Terunori Fujita; Shigekazu Matsui; Toshihiro Takai; Hideto Matsuoka; Akifumi Kagayama; Hiroshi Kuroda; Masayasu Ishibashi; Hiroshi Iwasaki; Nobuya Hirokane, all of Yamaguchi, Japan

[73] Assignee: Mitsui Chemicals, Inc., Tokyo, Japan

[21] Appl. No.: 09/291,988

[22] Filed: Apr. 15, 1999

Related U.S. Application Data

[62] Division of application No. 09/172,653, Oct. 15, 1998.

[30] Foreign Application Priority Data

Feb. 28, 1995 [JP] Japan ........................... 7-40578
Mar. 14, 1995 [JP] Japan ........................... 7-54818
May 24, 1995 [JP] Japan .......................... 7-125124

[51] Int. Cl.⁷ .................. C07D 487/22; C07C 45/32
[52] U.S. Cl. ................ 540/472; 540/473; 568/342; 568/568; 568/565
[58] Field of Search .................. 540/472, 473; 568/342, 568, 565

[56] References Cited

U.S. PATENT DOCUMENTS 4,459,427  7/1984  Middleton et al. .................. 568/342
5,847,227  12/1998  Fujita et al. ........................ 568/399

FOREIGN PATENT DOCUMENTS 439387A    7/1991  European Pat. Off. .
543619A1   5/1993  European Pat. Off. .
50-37741   4/1975  Japan .
1205835    9/1970  United Kingdom .
543619A1   5/1993  United Kingdom .

OTHER PUBLICATIONS

Chemical Abstracts, vol. 78, No. 21, Abstract No. 135806, XP002032832, Columbus, Ohio, US; May 28, 1973.
Database WPI Week 7534, AN 75–56360, XP002032834, Derwent Publications Ltd., London, GB, Apr. 8, 1975.
Chemical Abstracts, vol. 79, No. 9, Abstract No. 52880, XP002032833, Columbus, Ohio, US; Sep. 3, 1973.
Chemistry Letters, vol. 2, pp. 103–106, HARA et al..: "Oxidation of Cumene", 1973.

*Primary Examiner*—Mukund J. Shah
*Assistant Examiner*—Pavanaram K Sripada
*Attorney, Agent, or Firm*—Birch, Stewart, Kolasch & Birch, LLP

[57] ABSTRACT

A method for producing aryl alkyl hydroperoxides which comprises selectively oxidizing an aryl alkyl hydrocarbon having the formula:

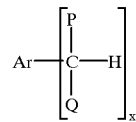

wherein P and Q are hydrogen or an alkyl and may be the same or different from each other; x is an integer of 1–3; and Ar is an aromatic hydrocarbon group having a valence of x, with an oxygen-containing gas in the presence of a transition metal complex which contains, as a ligand, a cyclic polyfunctional amine compound having at least three nitrogen atoms in the ring forming molecular chain or an open chain polyfunctional amine compound having at least three nitrogen atoms in the main chain of the molecule.

4 Claims, No Drawings

METHOD FOR PRODUCING ARYL AKLYL HYDROPEROXIDES

This application is a divisional of copending application Ser. No. 09/172,653, filed on Oct. 15, 1998, the entire contents of which are hereby incorporated by reference.

FIELD OF THE INVENTION

This invention relates to a method for producing aryl alkyl hydroperoxides by selectively oxidizing aryl alkyl hydrocarbons to their corresponding aryl alkyl hydroperoxides in high concentrations with oxygen containing gases in the presence of a transition metal complex catalyst which contains, as a ligand, a cyclic or an open chain polyfunctional organic amine compound having at least three nitrogen atoms in the molecule. The invention further relates to such transition metal complexes.

The aryl alkyl hydroperoxides are useful starting materials for the production of a number of commercial chemicals, for example, for the production of phenol and acetone from cumene monohydroperoxide.

DESCRIPTION OF THE PRIOR ART

There are already known a number of methods for the production of aryl alkyl hydroperoxides by oxidizing aryl alkyl hydrocarbons to their corresponding aryl alkyl hydroperoxides with oxygen containing gases in the presence of a catalyst.

For example, a method is disclosed in Japanese Patent Publication No. 50-50020 in which alkylbenzenes which have secondary alkyl groups such as 3,5-dimethylcumene are oxidized in the presence of water with an oxygen containing gas using a water soluble complex or chelate compound of cobalt, nickel, manganese, copper or iron having polyaminocarboxylic acids such as ethylenediaminetetraacetic acid (EDTA) as ligands to provide their corresponding aryl alkyl hydroperoxides.

According to this method, it is necessary that an alkali is added successively to an aqueous solution in which the reaction is carried out in the presence of the catalyst to adjust the solution at a slightly acetic pH so that the by-product of oxalic acid or acetic acid which deactivates the catalyst is prevented. Moreover the method has a further disadvantage that the oxidation reaction does not proceed at a practical rate at such relatively low temperatures as about 80° C. at which the thermal decomposition of the resulting organic hydroperoxides can be neglected.

SUMMARY OF THE INVENTION

It is an object of the invention to provide a method for producing aryl alkyl hydroperoxides by selectively oxidizing aryl alkyl hydrocarbons to their corresponding aryl alkyl hydroperoxides in high concentrations and in restraint of thermal decomposition of the resulting hydroperoxides with oxygen containing gases using a certain transition metal complex catalyst.

The invention provides a method for producing aryl alkyl hydroperoxides which comprises selectively oxidizing an aryl alkyl hydrocarbon having the formula (I):

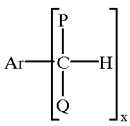

(I)

wherein P and Q are hydrogen or an alkyl and may be the same or different from each other; x is an integer of 1–3; and Ar is an aromatic hydrocarbon group having a valence of x, with an oxygen-containing gas in the presence of a transition metal complex catalyst which contains, as a ligand, a cyclic polyfunctional amine compound having at least three nitrogen atoms in the ring forming molecular chain or an open chain polyfunctional amine compound having at least three nitrogen atoms in the main chain of the molecule.

DESCRIPTION OF PREFERRED EMBODIMENTS

1. Starting Aryl Alkyl Hydrocarbons

The aryl alkyl hydrocarbon (I) used as a starting material in the method of the invention has the formula (I):

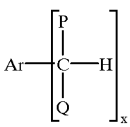

(I)

wherein P and Q are hydrogen or an alkyl and may be the same or different from each other; x is an integer of 1–3; and Ar is an aromatic hydrocarbon group having a valence of x.

It is necessary that the aryl alkyl hydrocarbon has at least one alpha hydrogen in the molecule, and it is in particular preferred that the aryl alkyl hydrocarbon has a hydrogen bonded to a tertiary carbon atom. Accordingly, it is preferred in the formula (I) that at least one of P and Q is an alkyl, and more preferably, both are alkyls. The alkyl is preferably methyl. In turn, the aromatic group having a valence of x is such that it is derived from benzene, naphthalene, biphenyl or diphenylether, with the first two being preferred.

Preferred examples of the aryl alkyl hydrocarbon include, for example, diisopropylbenzenes such as cumene, cymene, m-diisopropylbenzene or p-diisopropylbenzene, triisopropylbenzenes such as 1,3,5-triisopropybenzene, ethylbenzene, sec.-butylbenzene; sec.-butylethylbenzene, isopropylnaphthalenes, diisopropylnaphthalenes such as 2,6-diisopropylnaphthalene, isopropylbiphenyls, diisopropylbiphenyls such as 4,4'-diisopropylbiphenyl. These aryl alkyl hydrocarbons are merely illustrative, and the invention is not specifically limited to these examples in the aryl alkyl hydrocarbons.

According to the invention, the aryl alkyl hydrocarbon is selectively oxidized to the corresponding aryl alkyl hydroperoxides with an oxygen-containing gas in the presence of a transition metal complex catalyst which contains, as a ligand, a cyclic polyfunctional amine compound having at least three nitrogen atoms in the ring forming molecular chain or an open chain polyfunctional amine compound having at least three nitrogen atoms in the main chain of the molecule.

In the following formulas which show preferred examples of transition metal complexes used in the present invention, the formulas in brackets are polyfunctional amine compounds, i.e., ligands.

2. Complex Catalysts Containing Cyclic Polyfunctional Amine Compounds as Ligands First, transition metal complex catalyst which contains as a ligand a cyclic polyfunctional amine compound will be described.

The first transition metal complex catalyst used in the invention is an electrically neutral complex and has the formula (II):

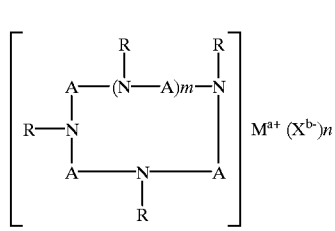

(II)

wherein A is independently an alkylene having 1–6 carbons in the main chain of the group, phenylene, naphthylene (naphthalenediyl), phenanthrylene (phenanthrenediyl), pyridinediyl, pyrrolediyl, pyrazinediyl, pyrimidinediyl or 1,3,5-triazinediyl, and may carry inactive substituents thereon; R is independently hydrogen, an alkyl, an aryl, an alkyl aryl or an aryl alkyl, and the alkyl, aryl, alkyl aryl or aryl alkyl may carry inactive substituents thereon; M is a central transition metal ion having a valence of +a; X is a counter ion having a valence of −b which is stable to oxidation, a is an integer of 1–4, b is a positive integer, n is an integer of 1–4, n is equal to a/b, and m is 0 or a positive integer of 1 or more.

In general, a transition metal complex catalyst may change in the oxidation number of the central metal ion during the oxidation of aryl alkyl hydrocarbon. For example, the oxidation number of the central metal ion may increase. In such a case, an anion present in the reaction medium will form a counter ion according to the increase of the oxidation number of the central metal ion.

In the above formula (II), A is independently an alkylene having 1–6 carbons in the main chain of the group, phenylene, naphthylene, phenanthrylene, pyridinediyl, pyrrolediyl, pyrazinediyl, pyrimidinediyl or 1,3,5-triazinediyl. The alkylene is exemplified by ethylene, trimethylene, tetramethylene, pentamethylene or hexamethylene, with ethylene being most preferred.

The groups represented by A may carry inactive substituents thereon, such as an alkyl, an alkoxyl, an aryl, an alkyl aryl, an aryl alkyl, an ethylene, an ether group, a cyano, an amino, an amido, a sulfonamide, a carboxyl, a carboxylate, a hydroxyl or an ester group.

R is independently hydrogen, an alkyl, an aryl, an alkyl aryl or an aryl alkyl, and the alkyl, aryl, alkyl aryl or aryl alkyl may thereon carry inactive substituents as mentioned hereinbefore.

The alkyl preferably has 1–25 carbons, and may be exemplified by methyl, ethyl, propyl, butyl, pentyl, hexyl, octyl, decyl, undecyl, dodecyl or tridecyl. The aryl may be exemplified by phenyl or naphthyl. The alkyl aryl may be exemplified by, for example, tolyl, whereas the aryl alkyl by, for example, benzyl.

The inactive substituent which R may carry thereon is exemplified, in particular, a hydroxyalkyl such as hydroxyethyl, hydroxypropyl or hydroxybutyl, an alkoxyalkyl such as methyoxyethyl, methoxypropyl, methoxybutyl or methoxypentyl, an ester group containing alkyl such as acetyloxyethyl, acetyloxypropyl, acetyloxybutyl, ethoxycarbonylethyl, ethoxycarbonylpropyl or ethoxycarbonylbutyl, a carboxyl or carboxylate group containing alkyl such as carboxymethyl, carboxyethyl, carboxypropyl, carboxybutyl, acetate, propionate or butyrate, a cyanoalkyl such as cyanomethyl, cyanoethyl, cyanopropyl or cyanobutyl, an aminoalkyl such as aminoethyl, aminopropyl, aminobutyl or aminopentyl, an amido group containing alkyl such as acetylaminomethyl, acetylaminoethyl, acetylaminopropyl, benzoylaminomethyl or benzoylaminopropyl, or a sulfonamide group containing alkyl such as methylsulfonaminoethyl, methylsulfonaminopropyl, methylsulfonaminobutyl, phenylsulfonaminoethyl, phenylsulfonaminobutyl, tolylsulfonaminoethyl or tolylsulfonaminopropyl.

It is particularly preferred that the cyclic polyfunctional amine compound which has three nitrogen atoms in the ring forming molecular chain (triazacrown) and which forms a ligand in the first transition metal complex has the formula (II) in which A is is an ethylene group. Preferred examples of such triazacrowns are the following compounds 1-01 to 1-18.

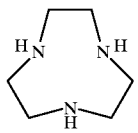

1-01

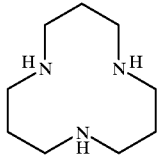

1-02

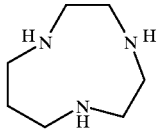

1-03

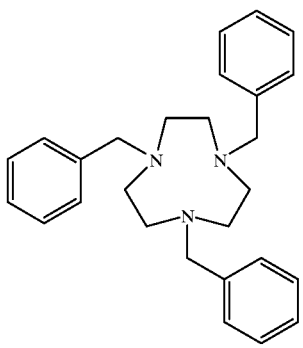

1-04

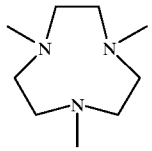

1-05

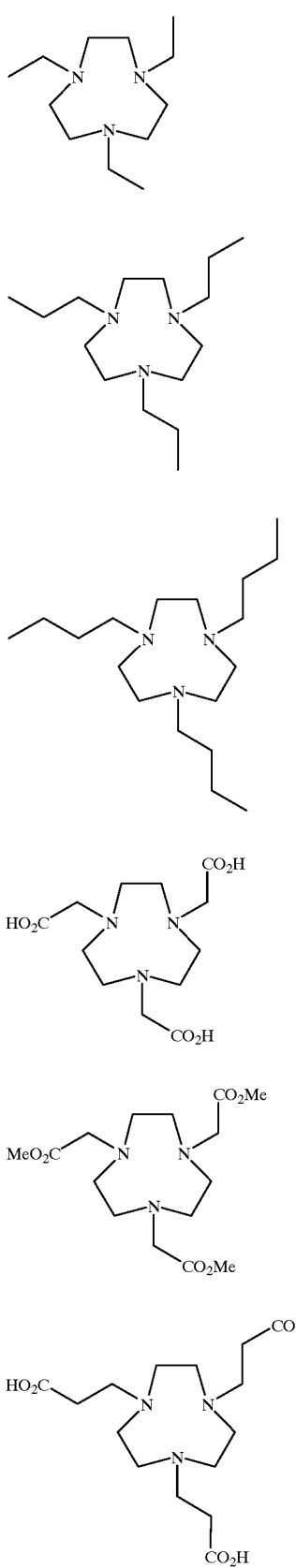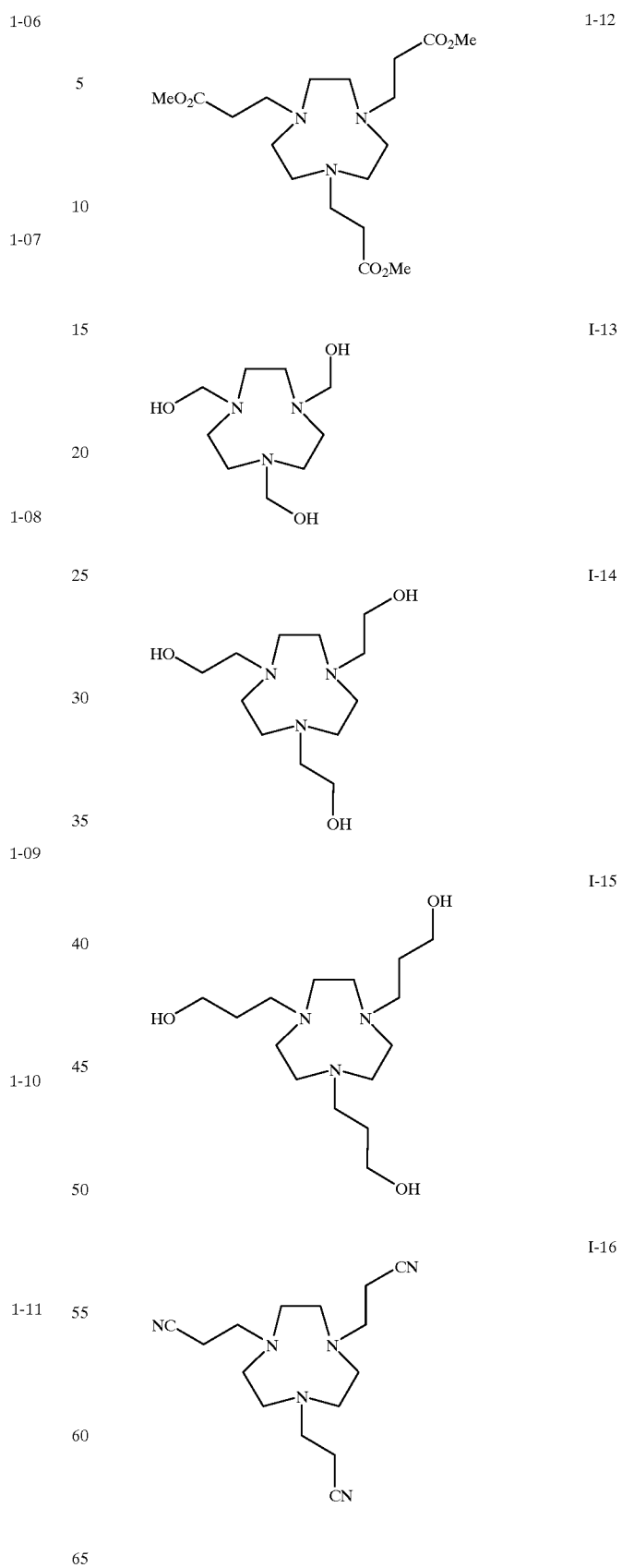

I-17

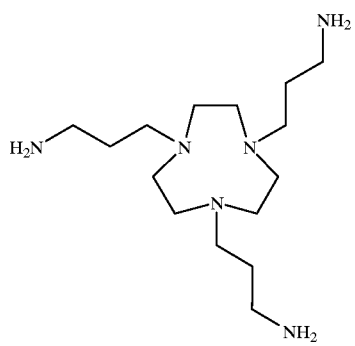

I-18

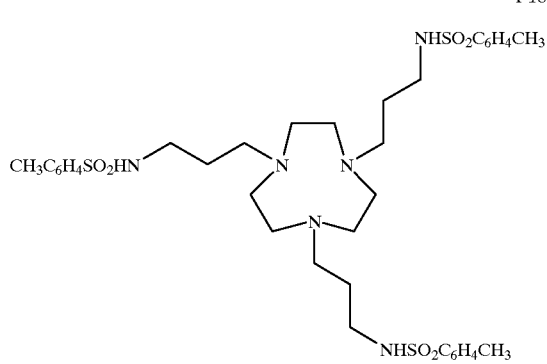

In turn, it is particularly preferred that the cyclic polyfunctional amine compound which has four nitrogen atoms or more in the ring forming molecular chain and which forms a ligand in the first transition metal complex has the formula (II) in which A is an ethylene, trimethylene, 2,6-pyridinediyl, 2,5-pyrrolediyl or 2,2'-bipyridyl-6,6'-diyl group and m is an integer of 1–4.

Preferred examples of such cyclic polyfunctional amine compounds are the following compounds 2-01 to 2-16 wherein R is an alkyl of 1–8 carbons, an aryl of 6–14 carbons such as phenyl, an aryl alkyl of 7–14 carbons such as benzyl, or an alkyl aryl of 7–14 carbons such as tolyl.

2-01

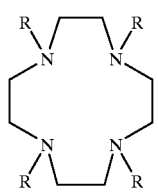

2-02

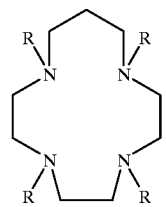

2-03

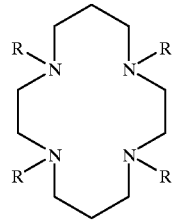

2-04

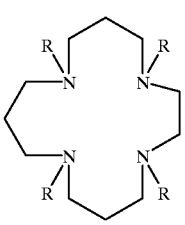

2-05

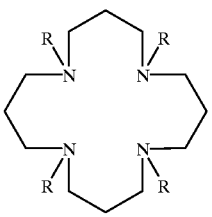

2-06

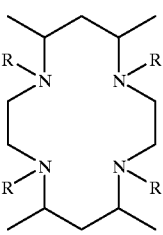

2-07

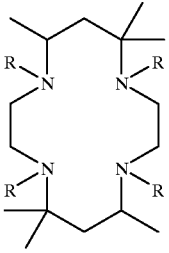

2-08

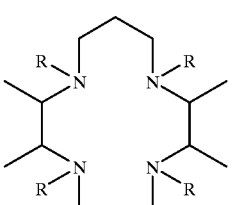

-continued 2-09
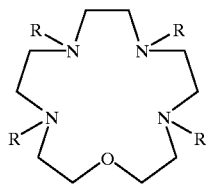

2-10
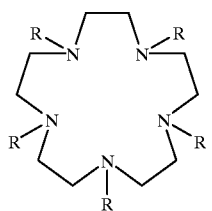

2-11
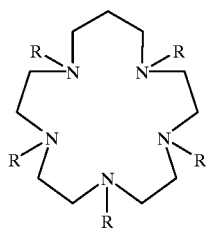

2-12
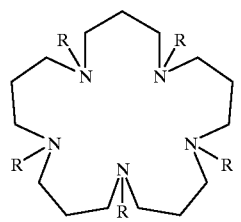

2-13
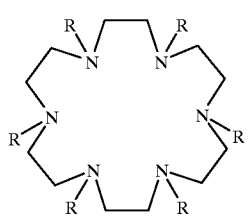

2-14
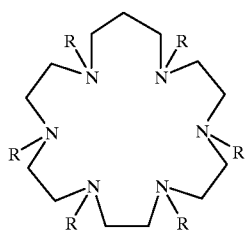

-continued 2-15
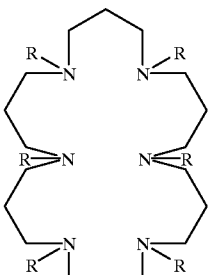

2-16
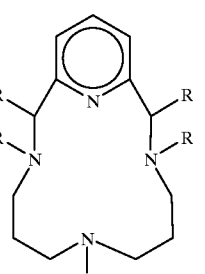

The second transition metal complex catalyst used in the invention has the formula (III):

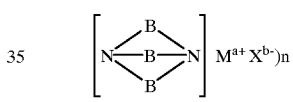  (III)

wherein B is a divalent organic group having the formula (IV):

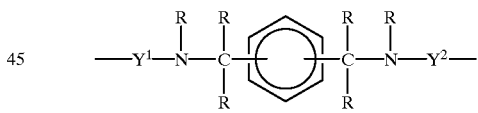

or

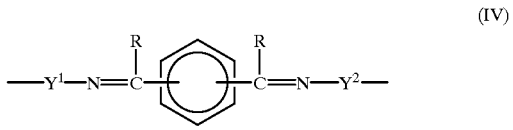  (IV)

wherein $Y^1$ and $Y^2$ are independently an alkylene having 1–6 carbons in the main chain of the group or phenylene, and may carry inactive substituents thereon; R is independently hydrogen, an alkyl, an aryl, an alkyl aryl or an aryl alkyl, and the alkyl, aryl, alkyl aryl or aryl alkyl may carry inactive substituents thereon; M is a central transition metal ion having a valence of 30 a; X is a counter ion having a valence of –b which is stable to oxidation; a is an integer of 1–4, b is a positive integer, n is an integer of 1–4, n is equal to a/b, and m is 0 or a positive integer of 1 or more.

It is particularly preferred that $Y^1$ and $Y^2$ are ethylene or trimethylene, and R is hydrogen. Accordingly, preferred examples of cyclic polyfunctional amine compounds which forms a ligand in the second transition metal complex (III) are the following compounds 3-01 to 3-08.

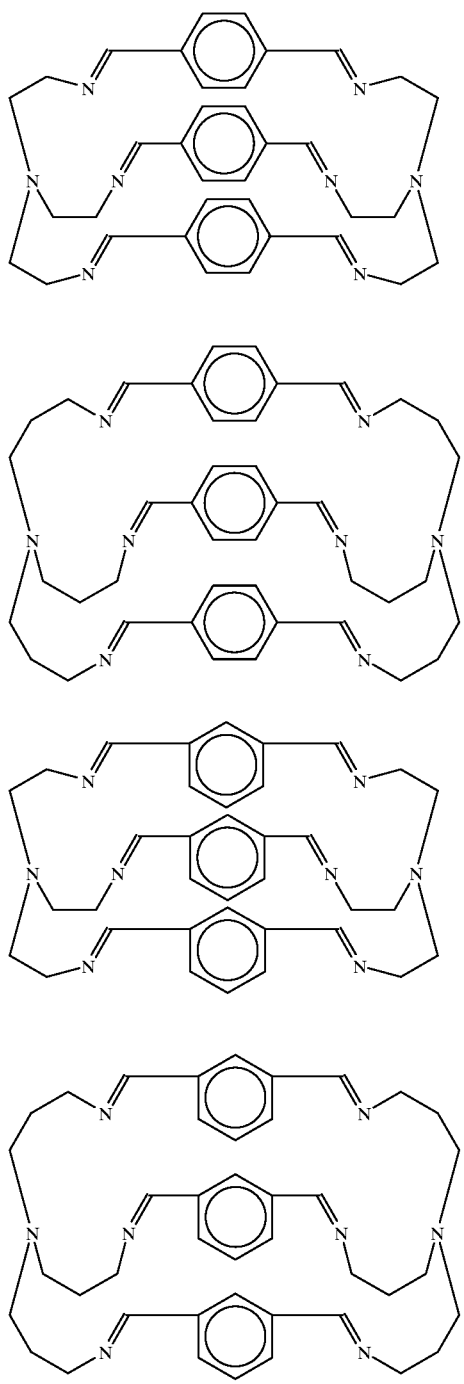
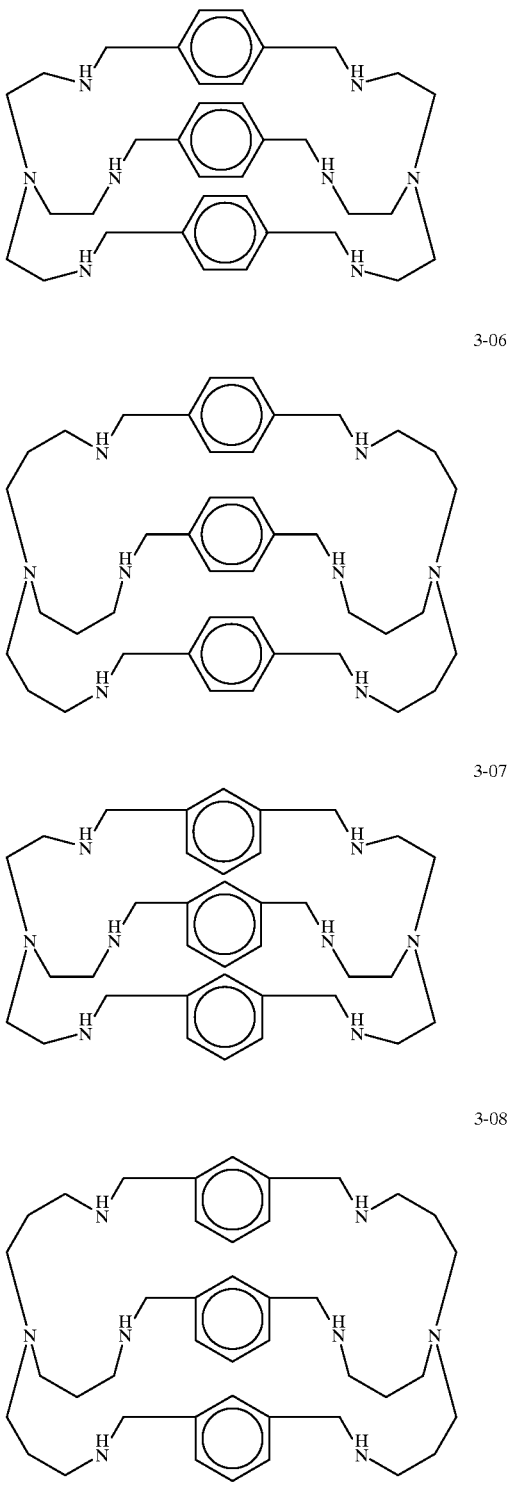

The third transition metal complex catalyst used in the invention has the formula (V):

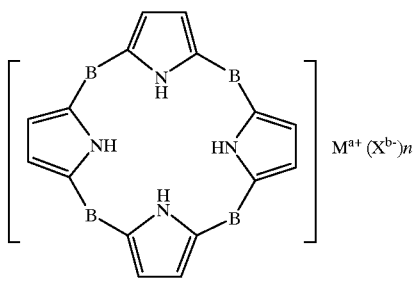

(V)

wherein B is an alkylene having 1–3 carbons in the main chain of the group and the alkylene and 2,5-pyrrolediyl may carry inactive substituents thereon as mentioned hereinbefore.

Most preferably, the cyclic plyfunctional amine compound is porphyrinogen or, alkyl or phenyl substituted porphyrinogen as represented by the formula (V) wherein B is methylene which may carry an alkyl or phenyl as an inactive substituent. Accordingly, preferred examples of such porphyrinogens are exemplified by the following compounds 4-01 to 4-09.

4-01

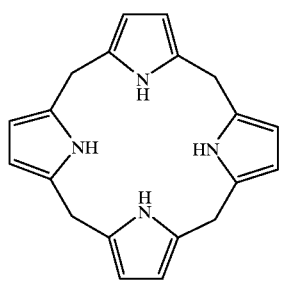

4-02

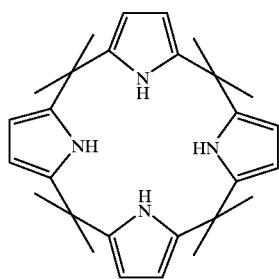

4-03

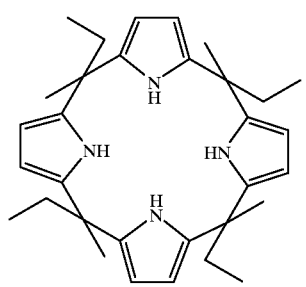

4-04

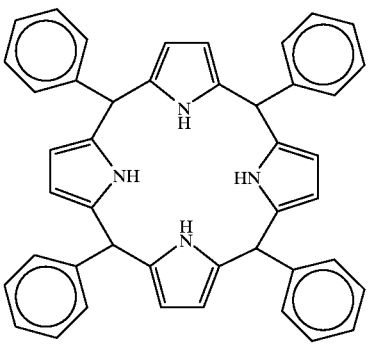

4-05

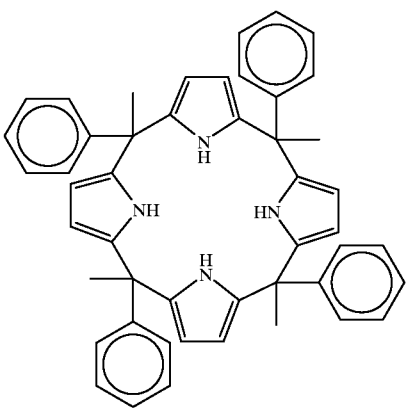

4-06

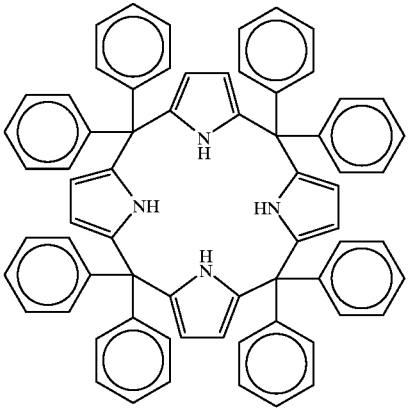

4-07

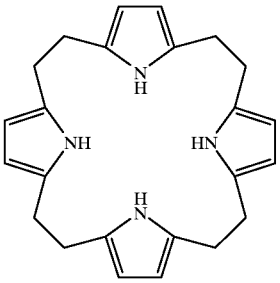

-continued

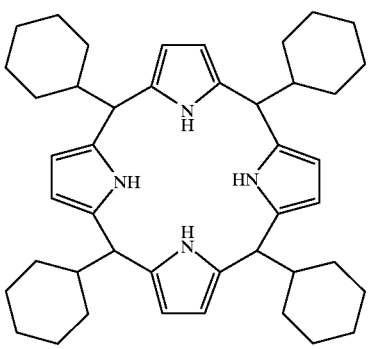
4-08

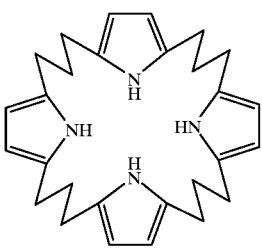
4-09

The fourth transition metal complex catalyst used in the invention has the formula (VI):

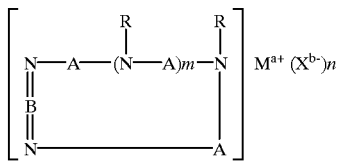
(VI)

wherein A is independently an alkylene having 1–6 carbons in the main chain of the group, phenylene, naphthylene, phenanthrylene, pyridinediyl, pyrroledyl, pyrazinediyl, pyrimidinediyl or 1,3,5-triazinediyl, and may carry inactive substituents thereon; B is a bis(alkylidene) having 2–10 carbons in the main chain of the group.

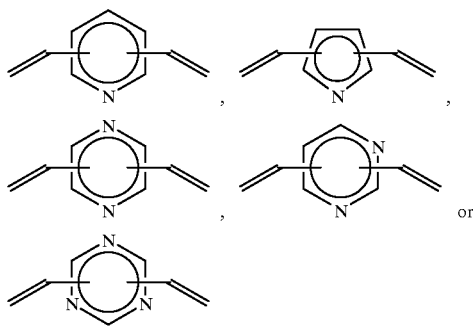

and may carry inactive substituents thereon; R is independently hydrogen, an alkyl, an aryl an alkyl aryl or an aryl alkyl, and the alkyl, aryl, alkyl aryl or aryl alkyl may carry inactive substituents thereon; M is a central transition metal ion having a valence of +a; X is a counter ion having a valence of −b which is stable to oxidation; a is an integer of 1–4, b is a positive integer, n is an integer of 1–4, n is equal to a/b, and m is 0 or a positive integer of 1 or more.

Preferred examples of the bis(alkylidene) group are as follows.

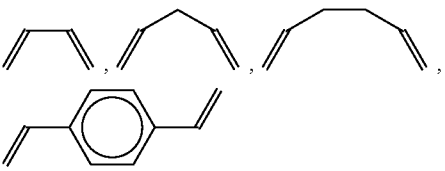

Preferred examples of further bis(alkylidene) groups which contain heteroaromatic rings therein are as follows:

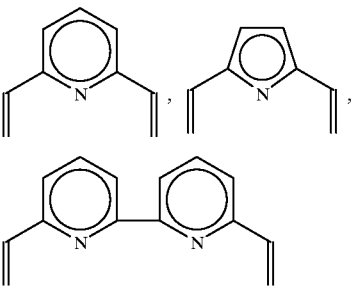

Accordingly, preferred examples of cyclic polyfunctional amine compounds are exemplified by the following compounds 5-01 to 5-04 wherein R is an alkyl of 1–8 carbons, an aryl of 6–14 carbons such as phenyl, an aryl alkyl of 7–14 carbons such as benzyl, or an alkyl aryl of 7–14 carbons such as tolyl 5-01
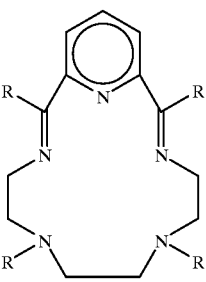

5-02
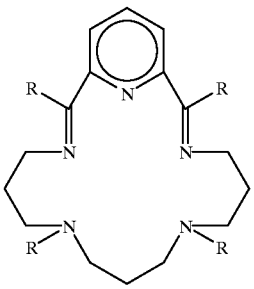

-continued

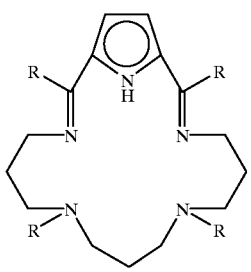

5-03

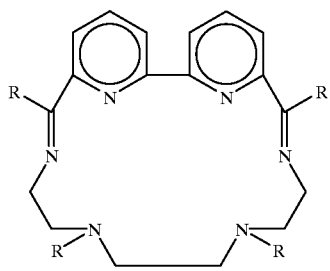

5-04

The fifth transition metal complex catalyst used in the invention has the formula (VII):

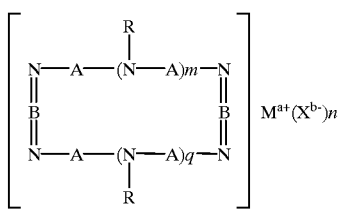

(VII)

wherein A is independently an alkylene having 1–6 carbons in the main chain of the group, phenylene, naphthylene, phenanthrylene, pyridinediyl, pyrrolediyl, pyrazinediyl, pyrimidinediyl or 1,3,5-triazinediyl, and may carry inactive substituents thereon; B is a bis(alkylidene) having 2–10 carbons in the main chain of the group.

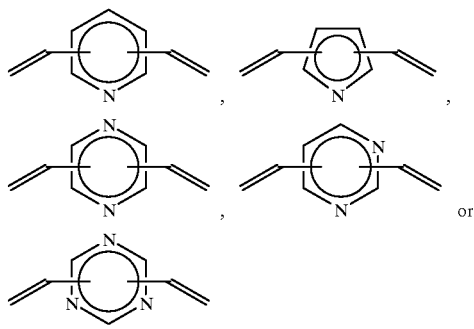

and may carry inactive substituents thereon; R is independently hydrogen, an alkyl, an aryl, an alkyl aryl or an aryl alkyl, and the alkyl, aryl, alkyl aryl or aryl alkyl may carry inactive substituents thereon; M is a central transition metal ion having a valence of +a; X is a counter ion having a valence of −b which is stable to oxidation; a is an integer of 1–4, b is a positive integer, n is an integer of 1–4, n is equal to a/b, and m is 0 or a positive integer of 1 or more.

Preferred examples of the bis(alkylidene) group may be the same as those mentioned in connection with the fourth transition metal complex hereinbefore.

Preferred examples of cyclic polyfunctional amine compounds are exemplified by the following compounds 6-01 to 6-04 wherein R is an alkyl of 1–8 carbons, an aryl of 6–14 carbons such as phenyl, an aryl alkyl of 7–14 carbons such as benzyl, or an alkyl aryl of 7–14 carbons such as tolyl.

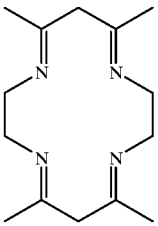

6-01

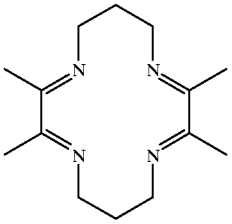

6-02

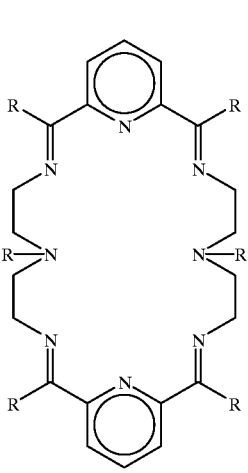

6-03

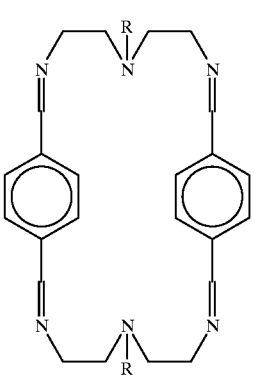

6-04

In any of the formulas of the transition metal complexes which contains, as a ligand, the cyclic polyfunctional amine compound as above mentioned, M is a central transition metal ion having a valence of +a wherein a is an integer of 1–4. Preferred examples of the transition metal is iron, nickel, manganese, cobalt, copper, chromium, ruthenium, rhodium, vanadium, titanium or zirconium, among which iron, nickel, manganese, cobalt, copper or ruthenium are particularly preferred.

X is a counter ion having a valence of −b which is stable to oxidation wherein b is a positive integer. Preferred examples of the counter ions are, for example, halide ions such as chloride ion or bromide ion, $SO_4^-$ (sulfate ion), $NO_3^-$, $BF_4^-$, $PF_6^-$, $ClO_4^-$, $CO_3^-$, $P_2O_7^{4-}$, $S_2O_6^{2-}$, organic carboxylic acid anions such as oxalate ion, acetate ion, trifluoroacetate ion, propionate ion, naphthenate ion, benzoate ion, naphthoate ion, organic sulfonic acid anions such as methanesulfonate ion, trifluoromethanesulfonate ion, benzenesulfonate ion or p-toluenesulfonate ion, or peroxide anions such as cumyl peroxide anion. Further examples include acetylacetonate or squarate ion.

In the formulas, a is an integer of 1–4, b is a positive integer, n is an integer of 1–4, n is equal to a/b, and m and, q, if any, is 0 or a positive integer of 1 or more, preferably 0, 1, 2 or 3.

According to the invention, the first transition metal complexes are particularly preferred. There may be mentioned as preferred examples in which the ligand or cyclic polyfunctional amine compound is a triazacrown, for example, (1,4,7-triazanonane)manganese(II) sulfate, (N,N',N"-tributyl-1,4,7-triazanonane)manganese(II) sulfate, (N,N',N"-tris(3-hydroxypropyl)-1,4,7-triazanonane) manganese (II) sulfate or

[N,N',N"-tris(potassium propioinate)-1,4,7-triazanonane) manganese(II) sulfate.

There may be mentioned as preferred examples in which the ligand or cyclic polyfunctional amine compound has four nitrogen atoms or more in the ring formation molecular chain, for example, (1,4,8,11-tetraazacyclotetradecane)manganese(II) sulfate, (1,4,8,11-tetraazacyclotetradecane)cobalt(III) chloride, (1,4,8,11-tetraazacyclotetradecane)copper (II) sulfate, (1,4,8,11-tetraazacyclotetradecane)ruthenium(II) chloride, (1,4,8,11-tetraazacyclotetradecane)nickel(II) sulfate, (1,4,8,11-tetraazacyclotetradecane)manganese(II) benzoate, (1,4,8,11-tetraazacyclotetradecane)cobalt(II) benzoate, (1,4,8,12-tetraazacyclotetradecane)manganese(II) sulfate,

[N,N',N",N'"-tetrakis(2-ethoxycarbonylethyl)-(1,4,8,11-tetraazacyclotetradecane]cobalt(II) sulfate,

[1,4,8,11-tetraazacyclotetradecane]manganese(II) stearate,

[1,4,8,11-tetraazacyclotetradecane]cobalt(II)stearate,

[N,N',N",N'"-tetra-n-butyl-(1,4,8,11-tetraazacyclotetradecane]manganese(II) sulfate.

Further examples are copper sulfate complexes, copper benzoate complexes, cobalt sulfate complexes, cobalt acetate complexes or ruthenium chloride complexes with one of the cyclic polyfunctional amine compound 3-01, 3-08, 4-01 to 4-09, 5-01 to 5-04 and 6-01 to 6-03.

3. Complex Catalysts Containing Open Chain Polyfunctional Amine Compounds as Ligands Now, transition metal complex catalysts which contain as a ligand an open chain polyfunctional amine compound will be described.

The first transition metal complex catalyst used has the formula(II):

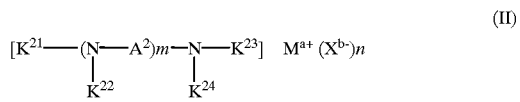

(II)

wherein $A^2$ is independently an alkylene having 1–6 carbons in the main chain of the group, o-phenylene, m-phenylene, p-phenylene, 1,8-naphthylene, 9,10-phenanthrylene, 2,6-pyridinediyl, 3,6-acrydinediyl, 2,2'-bipyridyl-6,6'-diyl, 1,10-phenanthroline-2,9-diyl, 2,6-pyrimidinediyl, 4,5-pyrimidinediyl, 2,6-pyrazinediyl, 2-phenyl-1,3,5-triazine-2,6-diyl,

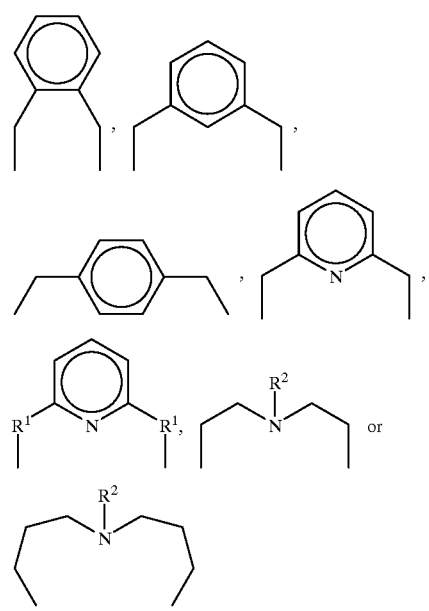

wherein $R^1$ is an alkylene of 1–8 carbons, and $R^2$ is an alkyl of 1–8 carbons, an aryl of 1–8 carbons, an aryl alkyl of 7–14 carbons or an alkyl aryl of 7–14 carbons, and $R^1$ and $R^2$ may carry inactive substituents thereon; $K^{21}$, $K^{22}$, $K^{23}$ and $K^{24}$ are independently hydrogen, an alkyl, an aryl, an alkyl aryl, an aryl alkyl, pyridyl, a pyridyl alkyl or quinolyl, wherein the alkyl, aryl, alkyl aryl, aryl alkyl, pyridyl, pyridyl alkyl or quinolyl may carry inactive substituents thereon; M is a central transition metal ion having a valence of +a; X is a counter ion having a valence of −b which is stable to oxidation; a is an integer of 1–4, b is a positive integer, n is an integer of 1–4, n is equal to a/b, and m is a positive integer of 2 or more.

In the above formula (II), $K^{21}$, $K^{22}$, $K^{23}$ and $K^{24}$ are independently hydrogen, an alkyl, an aryl, an aryl alkyl, pyridyl, a pyridyl alkyl or quinolyl.

The alkyl preferably has 1–25 carbons, and may be exemplified by methyl, ethyl, propyl, butyl, pentyl, hexyl, octyl, decyl, undecyl, dodecyl or tridecyl. The aryl may be exemplified by phenyl or naphthyl. The alkyl aryl may be exemplified by, for example, tolyl, whereas the aryl alkyl by, for example, benzyl.

The pyridyl may be exemplified by, for example, 2-pyridyl, 3-pyridyl or 6-methyl-2-pyridyl. The pyridyl alkyl may be exemplified by, for example, 2-pyridylmethyl, 3-pyridylmethyl, 2-pyridylethyl or 3-pyridylmethyl. The quinolyl may be 8-quinolyl.

The alkyl, aryl, alkyl aryl, aryl alkyl, pyridyl, pyridyl alkyl or quinolyl may carry inactive substituents thereon, such as a hydroxyl, an ether group, an ester group, a cyano, an amino, an amido, a sulfonamide, a carboxyl or a carboxylate.

$A^2$ is a group as mentioned above, and when it is an alkylene of 1–6 carbons, it may be ethylene, trimethylene, tetramethylene, pentamethylene or hexamethylene.

$A^2$ may also carry inactive substituents thereon, such as a hydroxyl, an ether group, an ester group, a cyano, an amino, an amido, a sulfonamide, a carboxyl or a carboxylate.

Preferred examples of the open chain polyfunctional amine compound which forms a ligand in the first transition metal complex (II) are the following compounds 5-01 to 5-25.

5-01: Diethylenetriamine
5-02: Triethylenetetramine
5-03: Tetraethylenepentamine
5-04: Pentaethylenehexamine
5-05: Hexaethyleneheptamine
5-06: Heptaethyleneoctamine
5-07: Octaethylenenonamine
5-08: N,N'-Bis(2-aminoethyl)-1,3-propanediamine
5-09: N-(3-aminopropyl)-1,3-propanediamine
5-10: N,N'-Bis(2-aminopropyl)-1,3-propanediamine
5-11: 1,5,9,13,17-Pentaazaheptadecane
5-12: 1,5,9,13,17,21-Hexaazaheneicosane
5-13: N,N,N',N'-Tetramethyltriethylenetetramine
5-14: N,N,N",N"-Tetramethyltriethylenetetramine
5-15: N,N,N",N"-Tetraethyltriethylenetetramine
5-16: N,N,N",N"-Tetrapropyltriethylenetetramine
5-17: N,N,N",N"-Tetrabutyltriethylenetetramine
5-18: N,N,N",N"-Tetrapentyltriethylenetetramine
5-19: N,N,N",N"-Tetrakis(2-cyanoethyl)triethylenetetramine
5-20: N,N,N",N"-Tetrakis(2-ethoxycarbonylethyl)triethylenetetramine
5-21: N,N,N",N"-Tetrakis(2-methoxycarbonylethyl)triethylenetetramine
5-22: N,N,N",N"-Tetrakis(3-hydroxypropyl)triethylenetetramine
5-23: N,N,N",N"-Tetrakis(3-tosylaminoethyl)triethylenetetramine
5-24: N,N,N",N"-Tetrakis(3-acetylaminopropyl)triethylenetetramine
5-25: N,N,N",N"'-Tetrakis(3-acetoxypropyl)triethylenetetramine In addition to the above compounds, 5-01 to 5-25, there may be mentioned the following examples of open chain polyfunctional amine compounds 5-26 to 5-29 and 11-01 to 11-70.

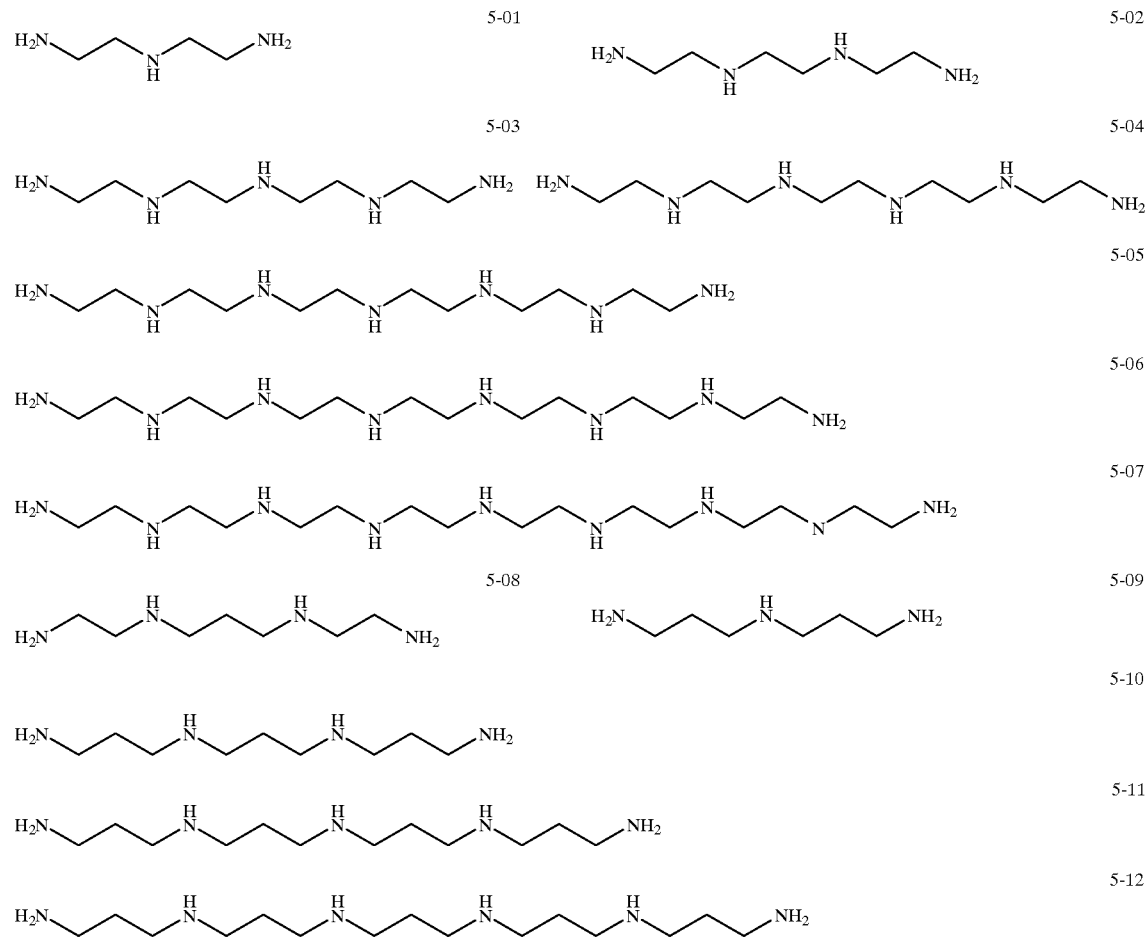

-continued
5-13
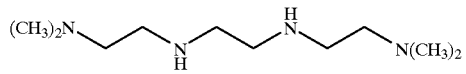
5-14
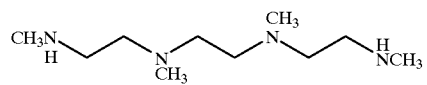
5-15
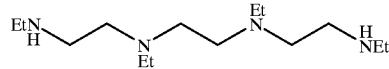
5-16
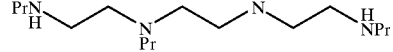
5-17
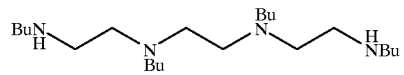
5-18
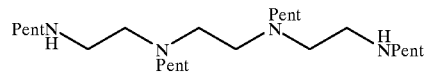
5-19
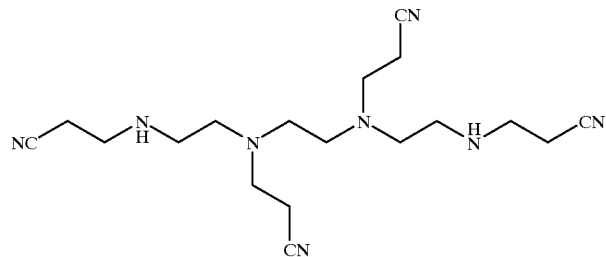
5-20
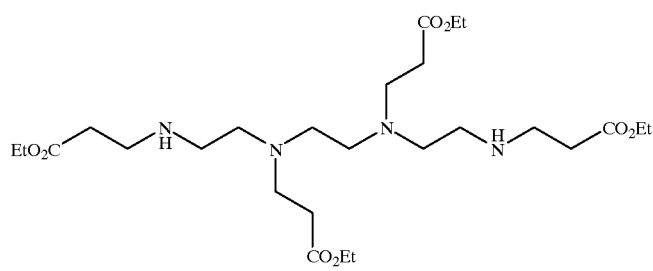
5-21
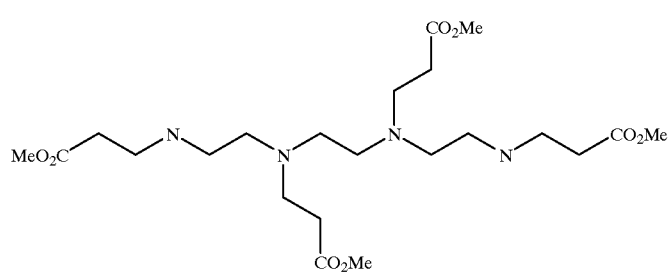
5-22
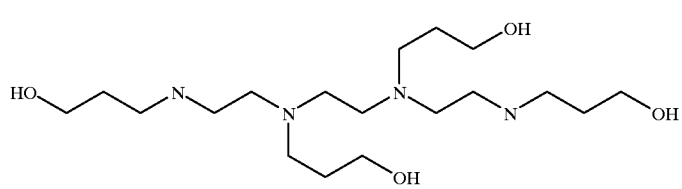
5-23
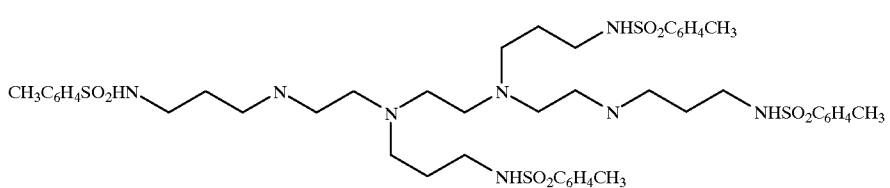

5-24
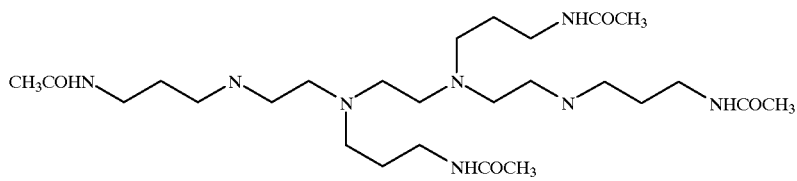
5-25
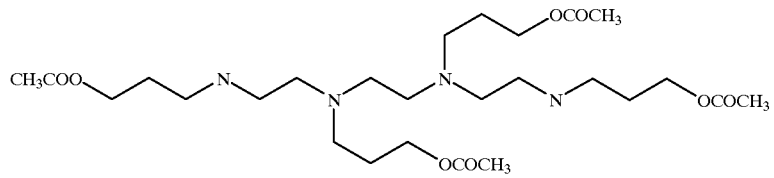
5-26
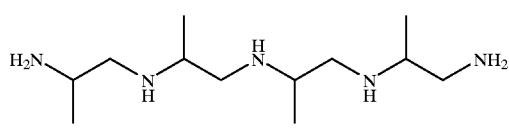
5-27
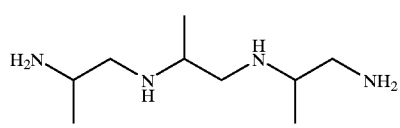
5-28
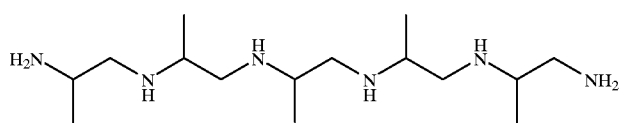
5-29
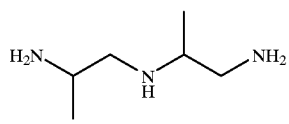
11-01
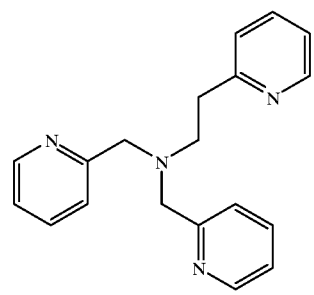
11-02
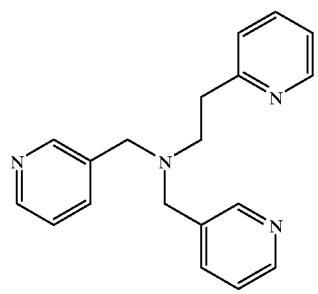
11-03
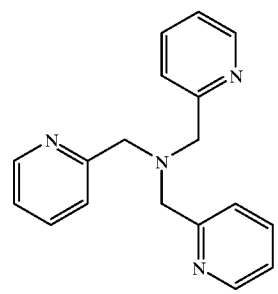

11-04
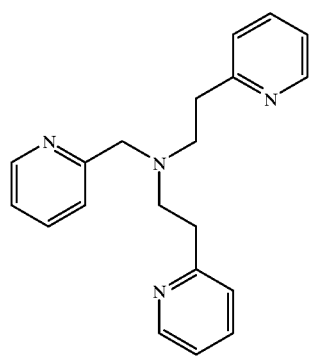
11-05
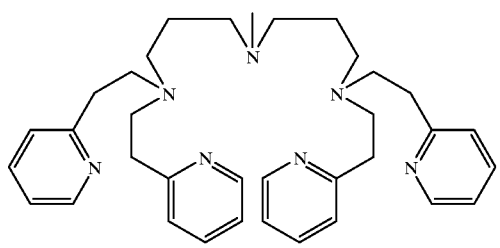
11-06
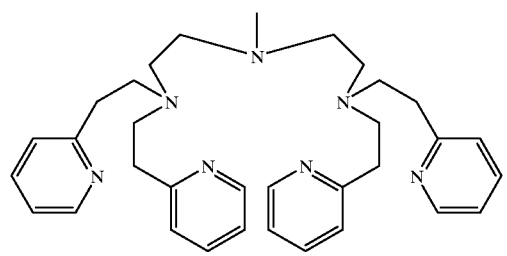
11-07
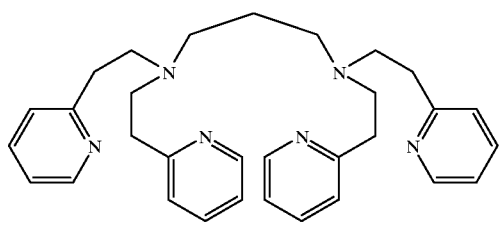
11-08
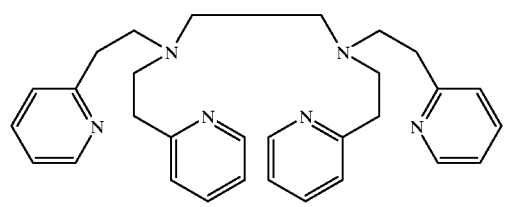
11-09
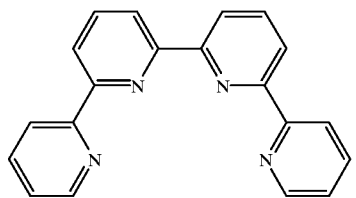
11-10
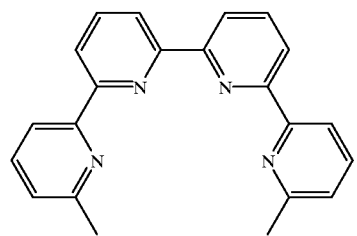
11-11
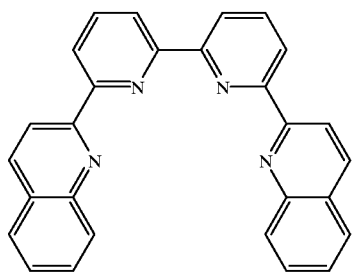
11-12
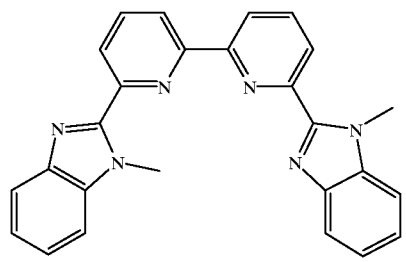
11-13
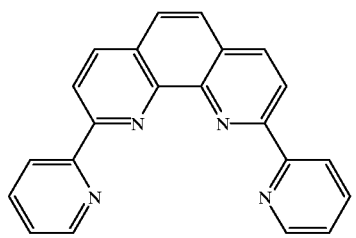

-continued
11-14
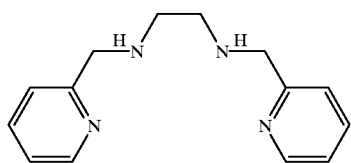
11-15
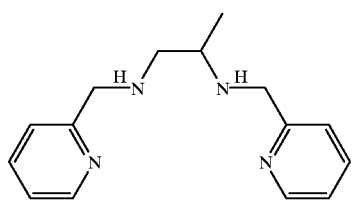
11-16
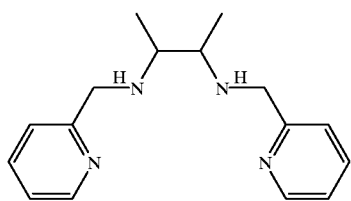
11-17
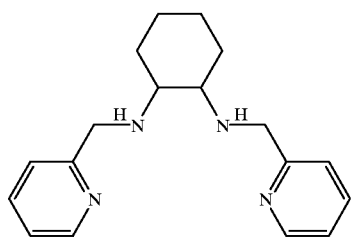
11-18
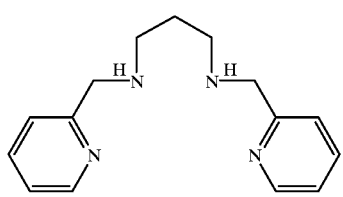
11-19
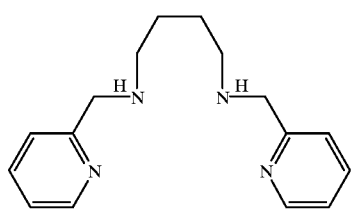
11-20
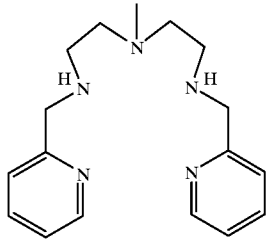
11-21
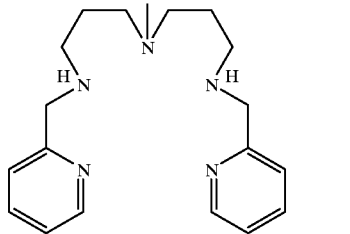
11-22
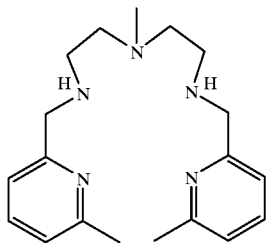
11-23
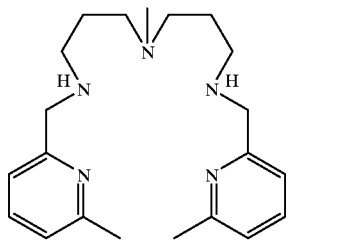
11-24
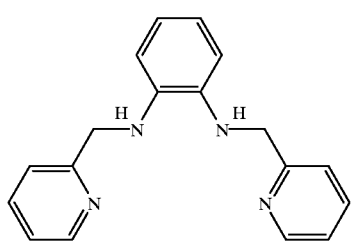
11-25
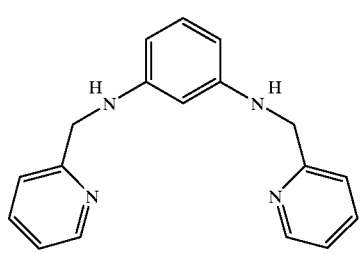

-continued
11-26
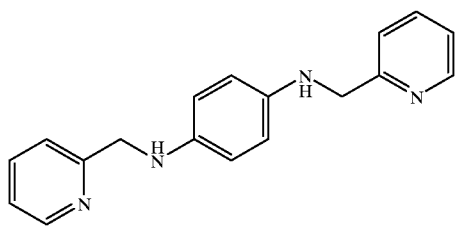
11-27
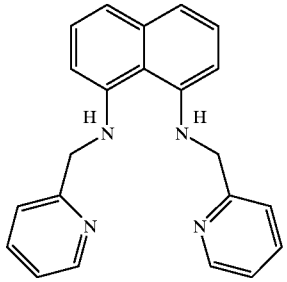
11-28
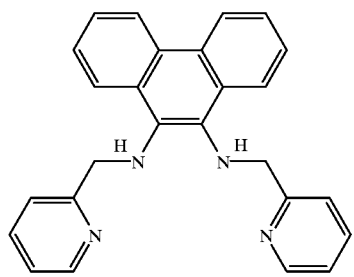
11-29
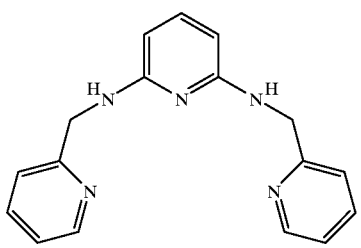
11-30
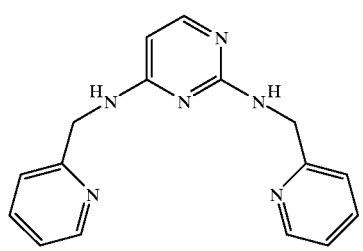
11-31
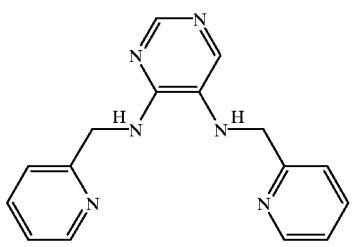
11-32
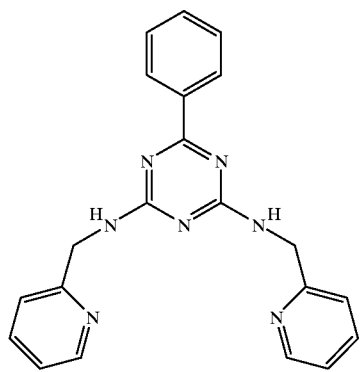
11-33
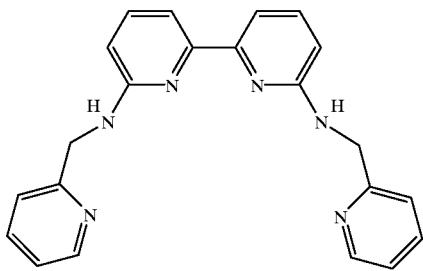
11-34
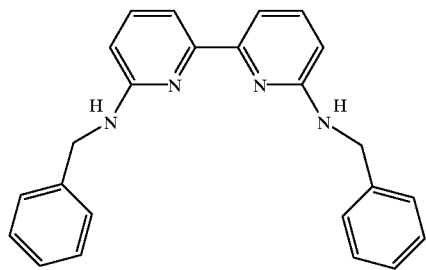
11-35
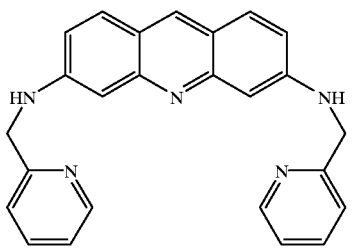

11-36
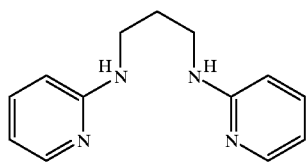
11-37
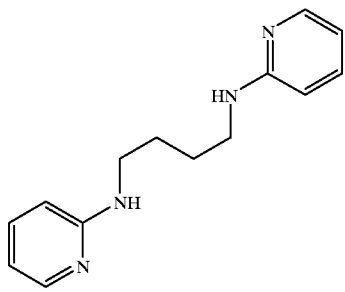
11-38
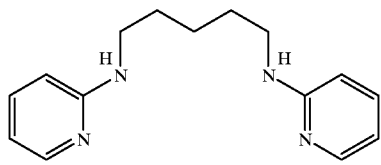
11-39
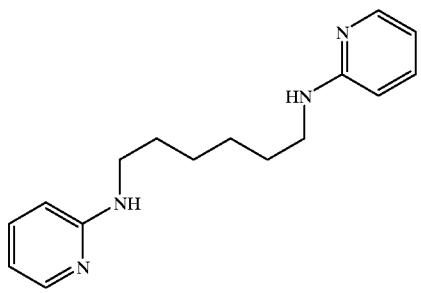
11-40
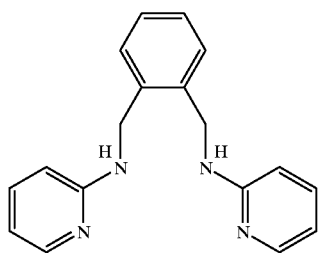
11-41
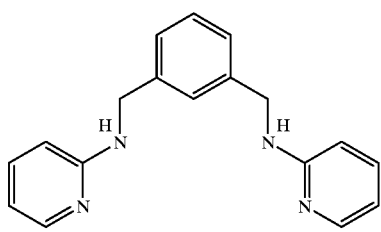
11-42
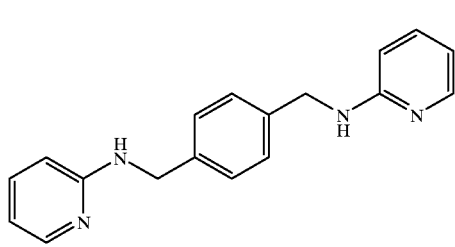
11-43
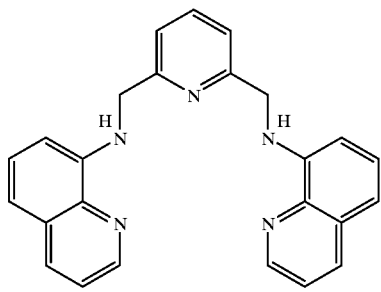
11-44
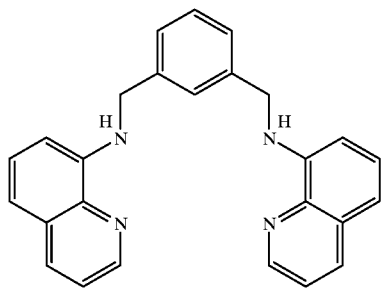
11-45
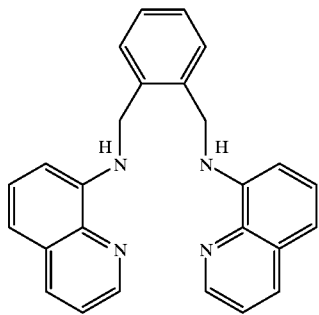

-continued
11-46
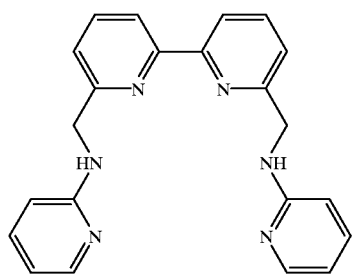
11-47
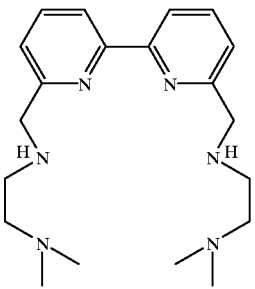
11-48
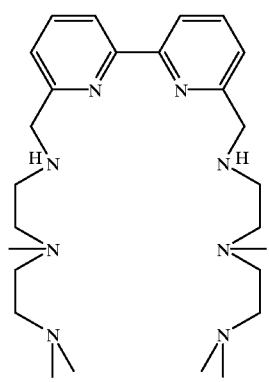
11-49
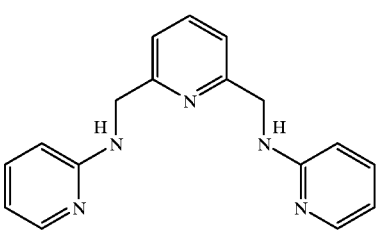
11-50
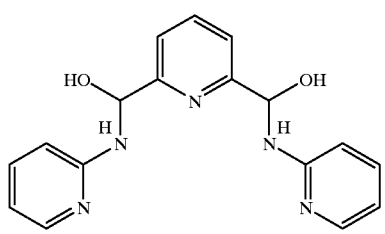
11-51
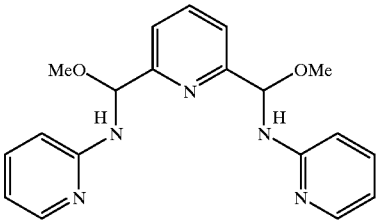
11-52
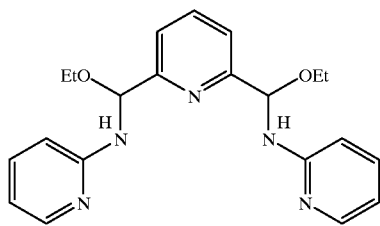
11-53
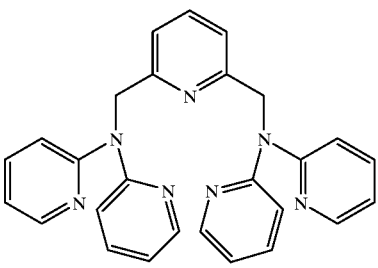
11-54
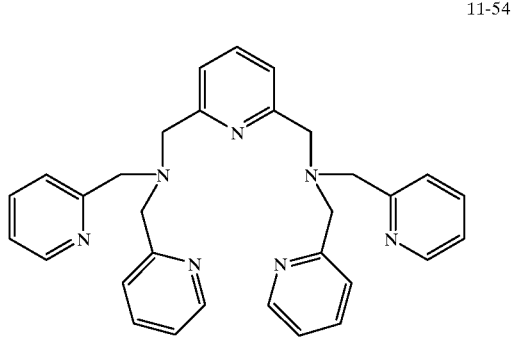
11-55
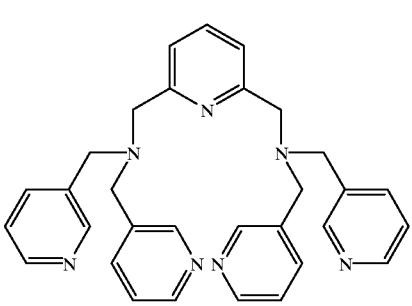

11-56
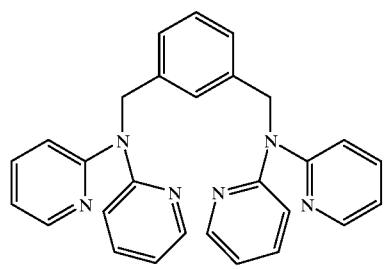
11-57
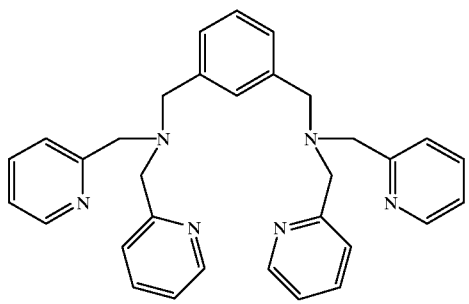
11-58
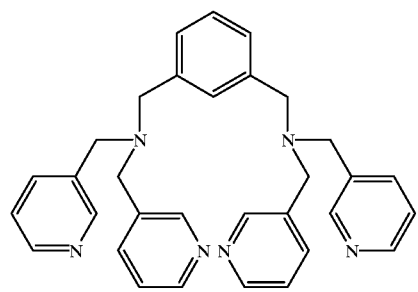
11-59
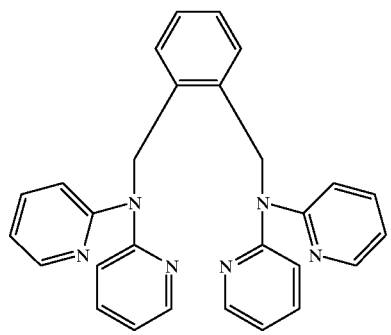
11-60
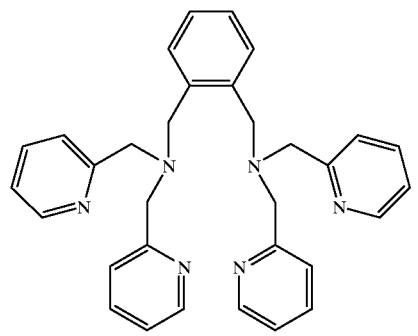
11-61
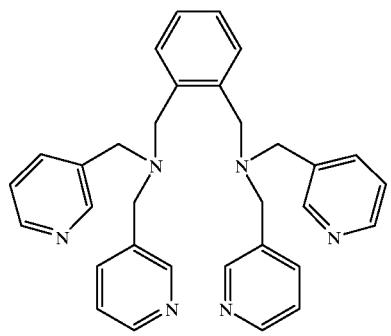
11-62
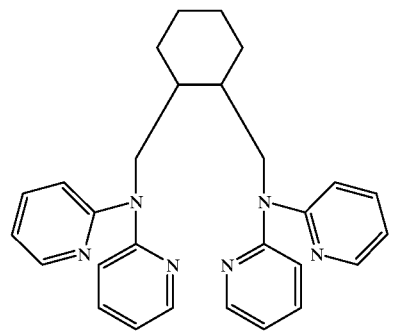
11-63
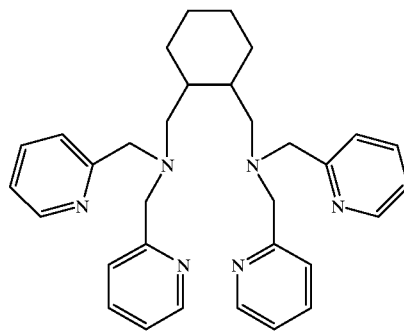

-continued 11-64
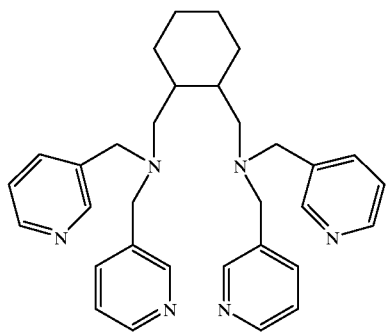

11-65
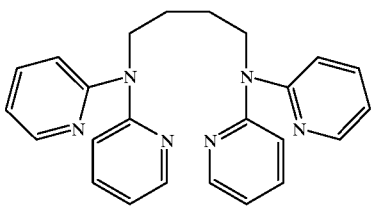

11-66
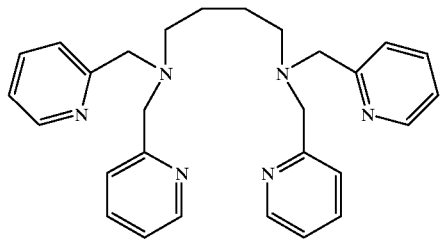

11-67
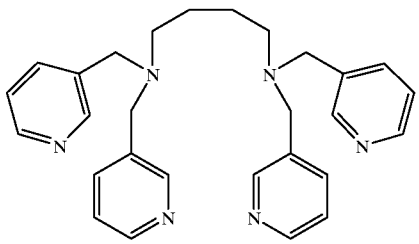

11-68
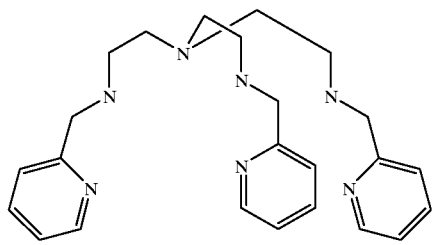

11-69
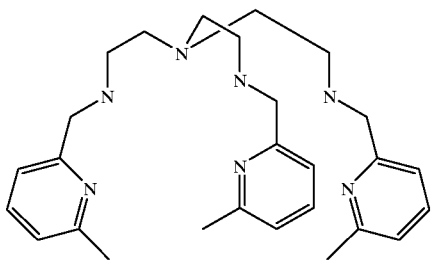

11-70
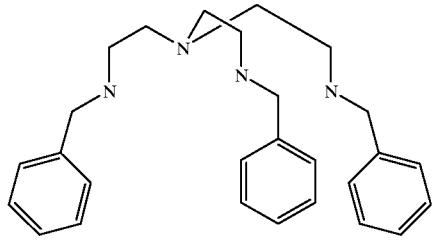

Among these are preferred amine compounds which have the formula (II) wherein $A^2$ is ethylene or trimethylene, and m is 2 or 3.

The second transition metal complex catalyst used has the formula (III):

$$[K^{31}=N-A^3-N=K^{32}]M^{a+}(X^{b-})n \qquad (III)$$

wherein $A^3$ is independently an alkylene having 1–6 carbons in the main chain of the group, o-phenylene, m-phenylene, p-phenylene, 1,8-naphthylene, 9,10-phenanthrylene, 2,6-pyridinediyl, 3,6-acrydinediyl, 2,2'-bipyridyl-6,6'-diyl, 1,10-phenanthroline-2,9-diyl, 2,6-pyrimidinediyl, 4,5-pyrimidinediyl, 2,6-pyrazinediyl, 2-phenyl-1,3,5-triazine-2,6-diyl,

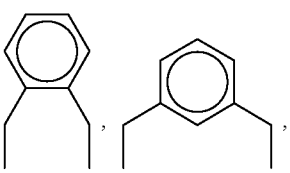

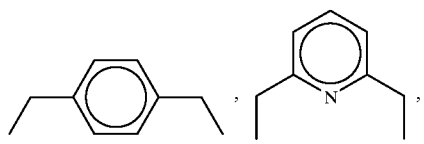 , 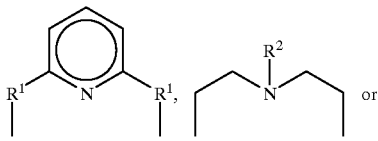 or 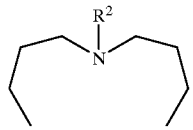

wherein $R^1$ is an alkylene of 1–8 carbons, and R is an alkyl of 1–8 carbons, an aryl of 1–8 carbons, an aryl alkyl of 7–14 carbons or an alkyl aryl of 7–14 carbons, and may carry inactive substituents thereon; $K^{31}$ and $K^{32}$ are 2-aminobenzylidene and may carry inactive substituents thereon; M is a central transition metal ion having a valence of +a; X is a counter ion having a valence of -b which is stable to oxidation; a is an integer of 1–4, b is a positive integer, n is an integer of 1–4, n is equal to a/b, and m is a positive integer of 2 or more.

Preferred examples of the open chain polyfunctional amine compound which forms a ligand in the second transition metal complex (III) are the following compounds 6-01 to 6-10.

6-01

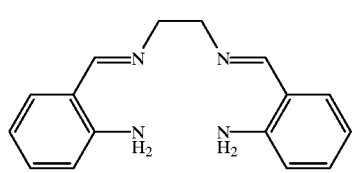

6-02

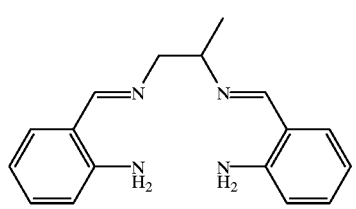

6-03

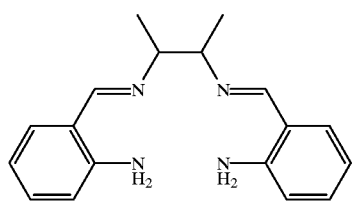

6-04

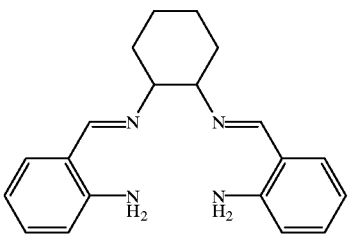

6-05

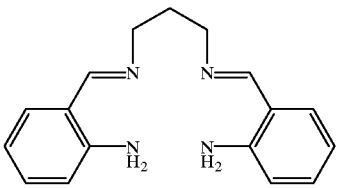

6-06

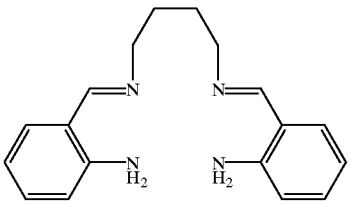

6-07

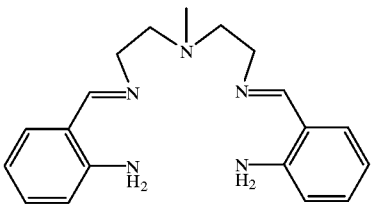

6-08

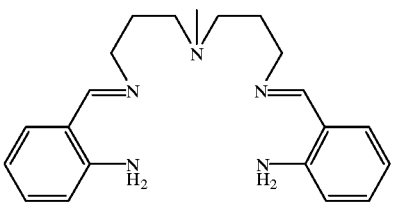

6-09

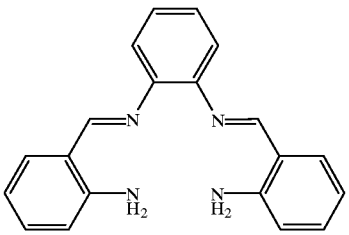

6-10

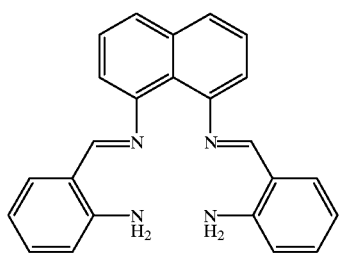

The third transition metal complex catalyst used has the formula (IV):

$$[K^{41}=N-A^4-N=K^{42}]M^{a+}(X^{b-})n \qquad (IV)$$

wherein $A^4$ is independently an alkylene having 1–6 carbons in the main chain of the group, o-phenylene, m-phenylene, p-phenylene, 1,8-naphthylene, 9,10-phenanthrylene, 2,6-pyridinediyl, 3,6-acrydinediyl, 2,2'-bipyridyl-6,6'-diyl, 1,10-phenanthroline-2,9-diyl, 2,6-pyrimidinediyl, 4,5-pyrimidinediyl, 2,6-pyrazinediyl, 2-phenyl-1,3,5-triazine-2,6-diyl,

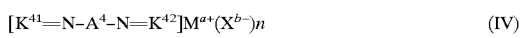

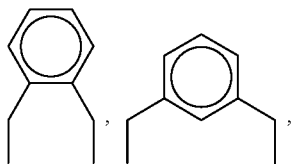

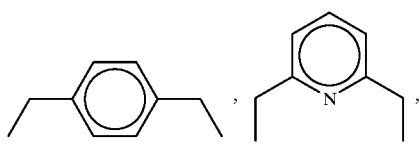 or

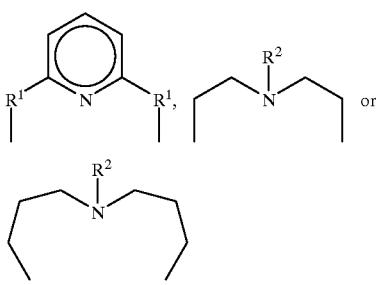

wherein $R^1$ is an alkylene of 1–8 carbons, and $R^2$ is an alkyl of 1–8 carbons, an aryl of 1–8 carbons, an aryl alkyl of 7–14 carbons or an alkyl aryl of 7–14 carbons, and may carry inactive substituents thereon; $K^{41}$ and $K^{42}$ are 2-pyridylmethylene or 6-methyl-2-pyridylmethylene and may carry inactive substituents thereon; M is a central transition metal ion having a valence of +a; X is a counter ion having a valence of −b which is stable to oxidation; a is an integer of 1–4, b is a positive integer, n is an integer of 1–4, n is equal to a/b, and m is a positive integer of 2 or more.

Preferred examples of the open chain polyfunctional amine compound which forms a ligand in the third transition metal complex (IV) are the following compounds 7-01 to 7-22.

7-01
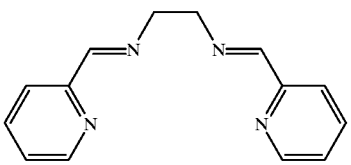

7-02
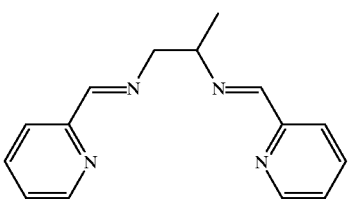

7-03
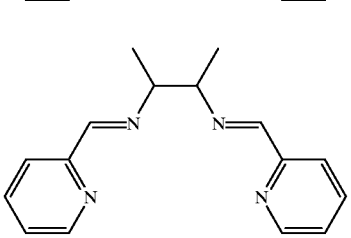

7-04
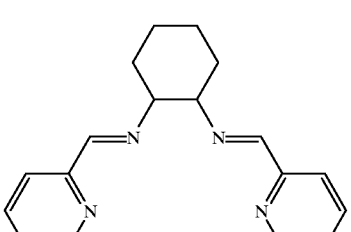

7-05
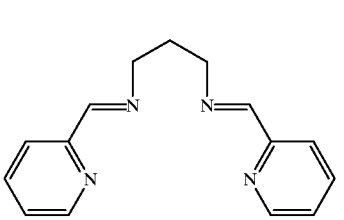

7-06
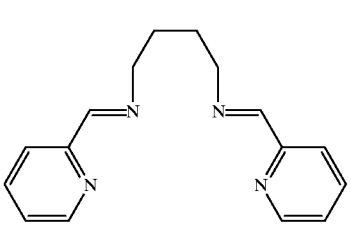

7-07
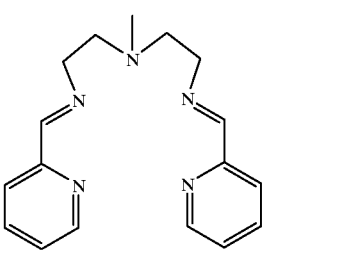

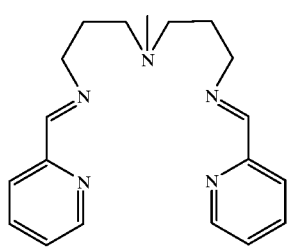 7-08
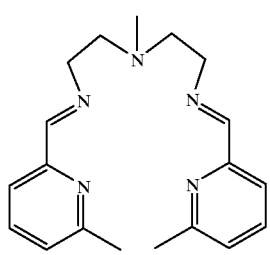 7-09
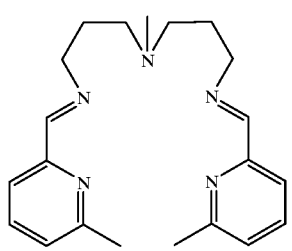 7-10
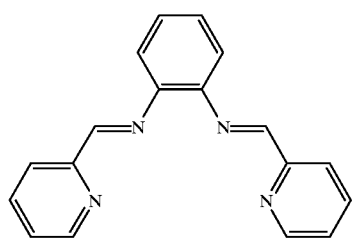 7-11
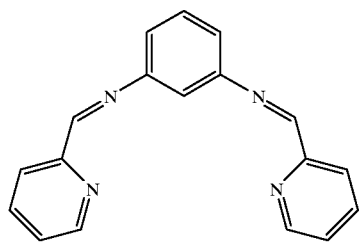 7-12
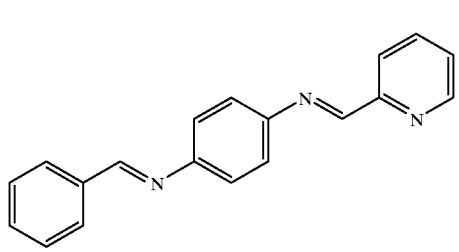 7-13
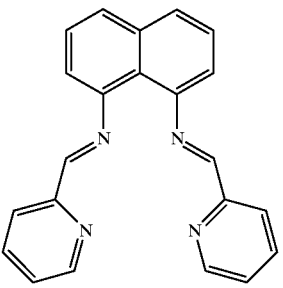 7-14
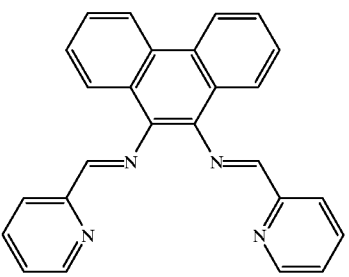 7-15
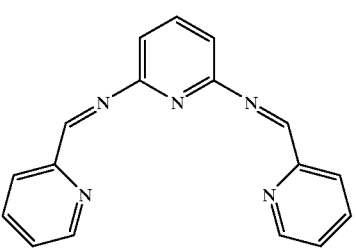 7-16
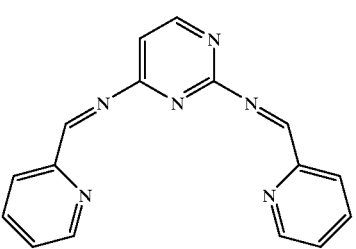 7-17
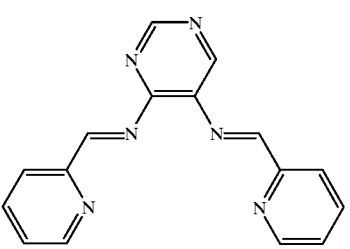 7-18

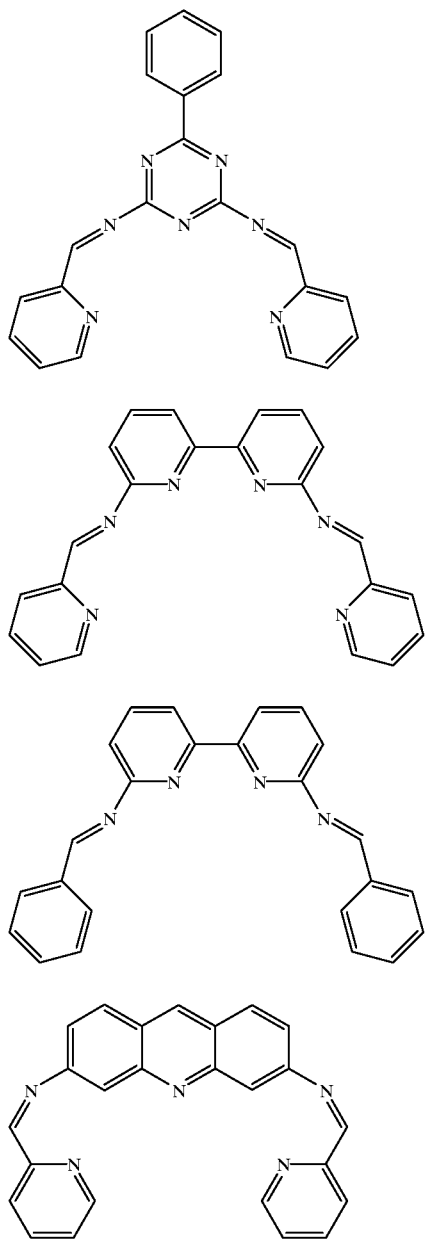

7-19

7-20

7-21

7-22

The fourth transition metal complex catalyst used has the formula (V):

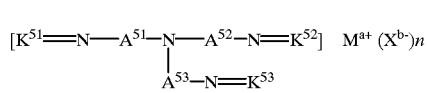

(V)

wherein $A^{51}$ to $A^{53}$ are independently an alkylene having 1–6 carbons in the main chain of the group and may carry inactive substituents thereon; $K^{51}$ to $K^{53}$ are benzylidene, 2-pyridylmethylene or 6-methyl-2-pyridylmethylene and may carry inactive substituents thereon; M is a central transition metal ion having a valence of +a; X is a counter ion having a valence of −b which is stable to oxidation; a is an integer of 1–4, b is a positive integer, n is an integer of 1–4, n is equal to a/b, and m is a positive integer of 2 or more.

Preferred examples of the open chain polyfunctional amine compound which forms a ligand in the fourth transition metal complex (V) are the following compounds 8-01 to 8-03.

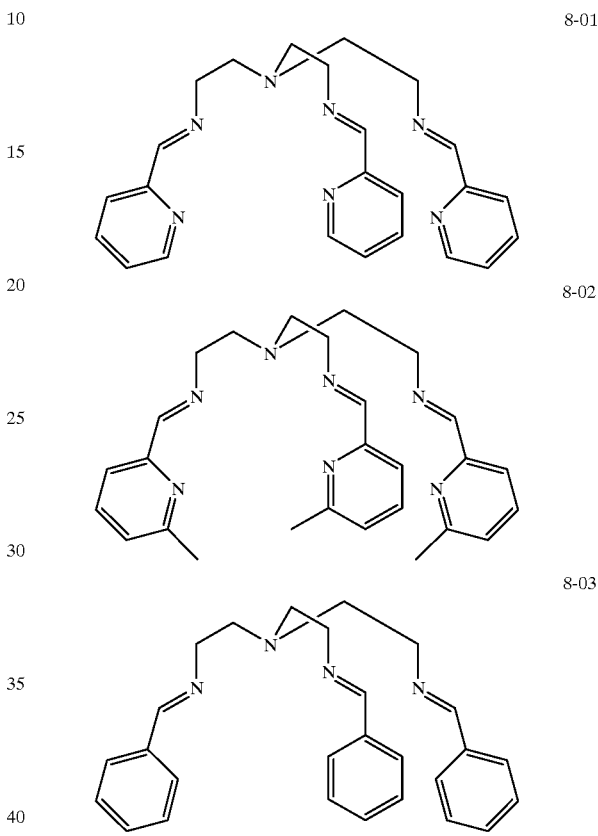

8-01

8-02

8-03

The fifth transition metal complex catalyst used has the formula (VI):

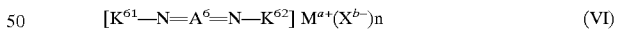

(VI)

wherein $A^6$ is

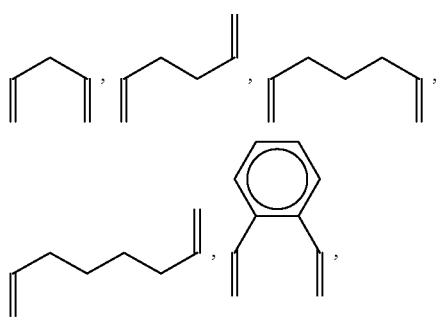

-continued

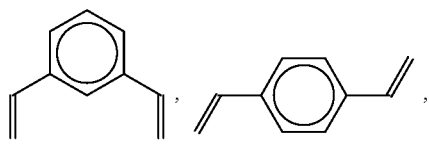,

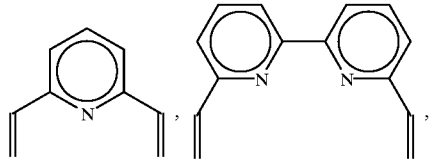,

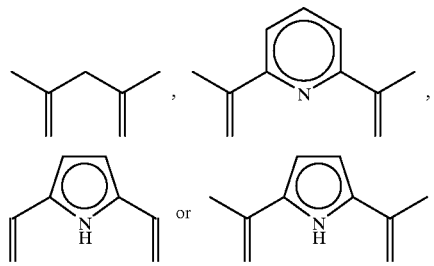

or and may carry inactive substituents thereon; $K^{61}$ and $K^{62}$ are 2-pyridyl, 3-pyridyl, 8-quinolyl or an aminoalkyl wherein the alkyl has 2–4 carbons and may carry inactive substituents thereon; M is a central transition metal ion having a valence of +a; X is a counter ion having a valence of –b which is stable to oxidation; a is an integer of 1–4, b is a positive integer, n is an integer of 1–4, n is equal to a/b, and m is a positive integer of 2 or more.

Preferred examples of the open chain polyfunctional amine compound which forms a ligand in the fifth transition metal complex (VI) are the following compounds 9-01 to 9-18.

9-01

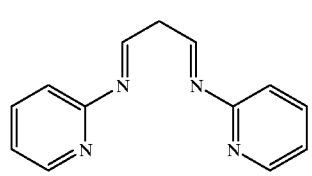

9-02

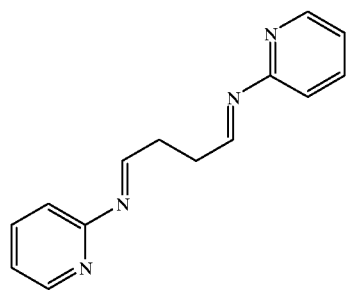

9-03

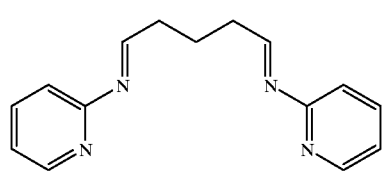

-continued 9-04

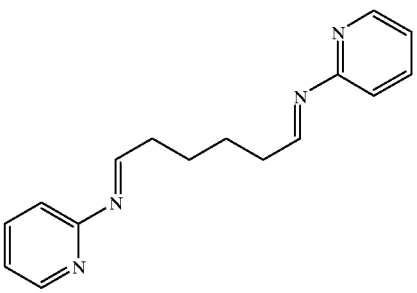

9-05

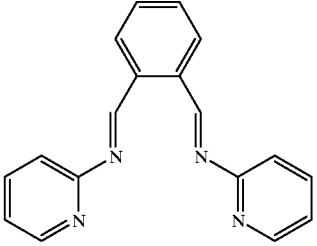

9-06

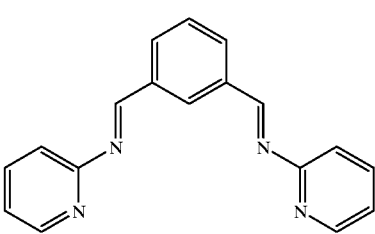

9-07

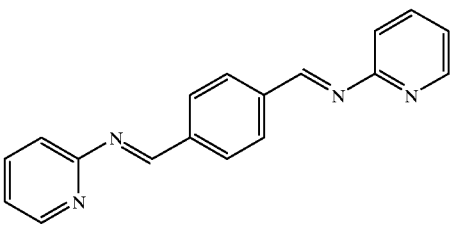

9-08

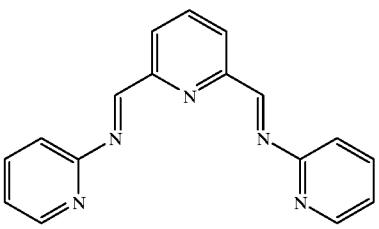

9-09

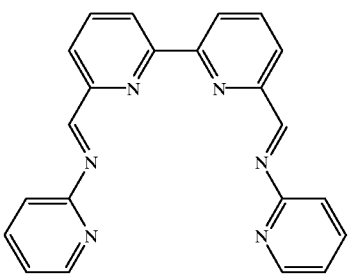

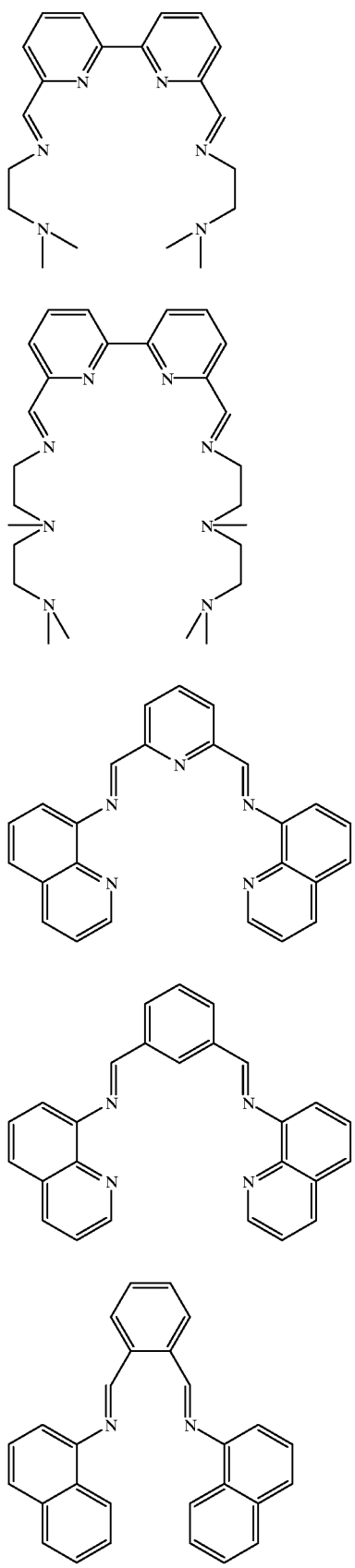

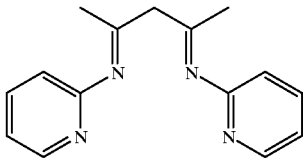

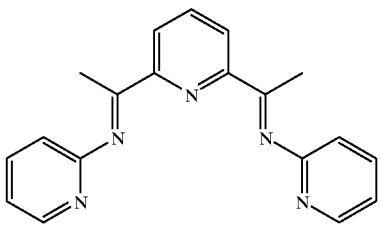

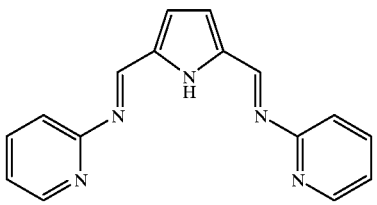

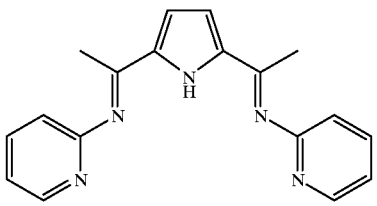

The sixth transition metal complex catalyst used has the formula (VII):

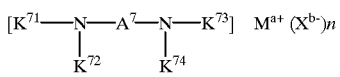

wherein $A^7$ is

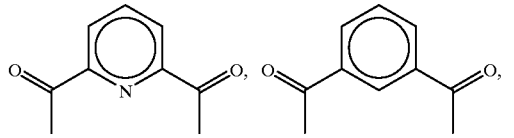

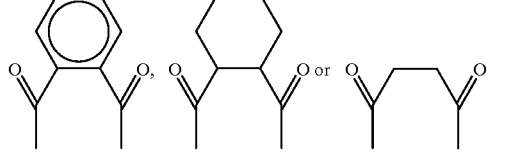

and may carry inactive substituents thereon; $K^{71}$ to $K^{74}$ are 2-pyridyl, 3-pyridyl, 2-pyridylmethyl or 3-pyridylmethyl and may carry inactive substituents thereon; M is a central transition metal ion having a valence of +a; X is a counter ion having a valence of −b which is stable to oxidation; a is an integer of 1–4, b is a positive integer, n is an integer of 1–4, n is equal to a/b, and m is a positive integer of 2 or more.
Preferred examples of the open chain polyfunctional amine compound which forms a ligand in the sixth transition metal complex (VI) are the following compounds 10-01 to 10-15.
10-01
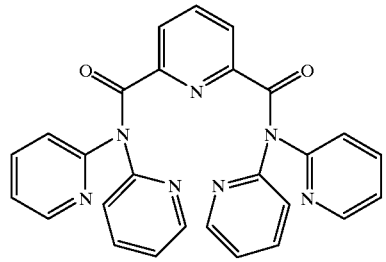
10-02
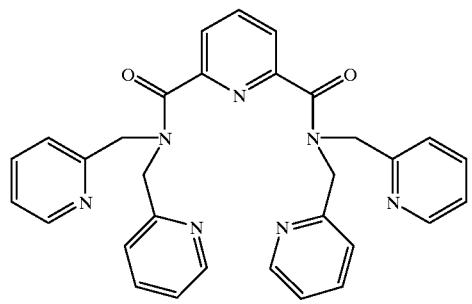
10-03
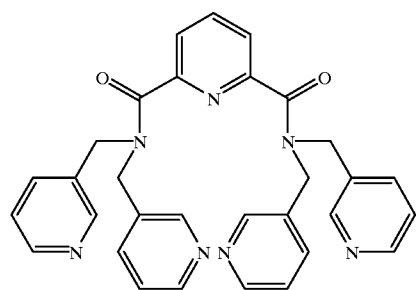
10-04
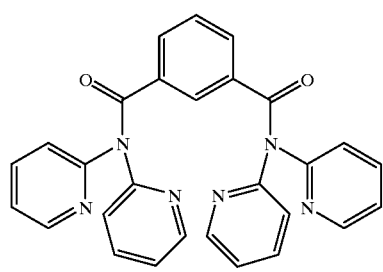
10-05
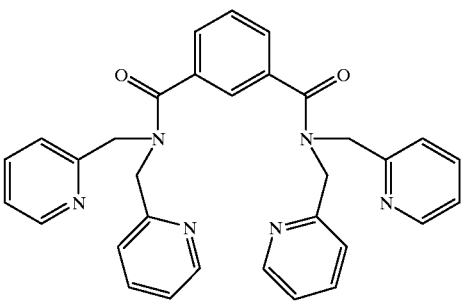
10-06
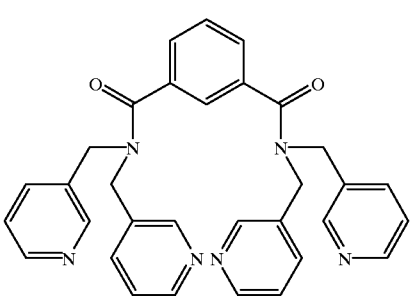
10-07
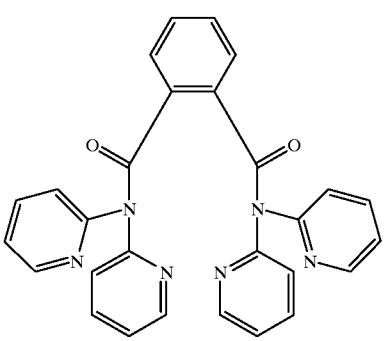
10-08
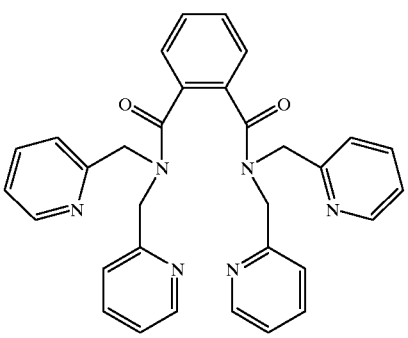

10-09
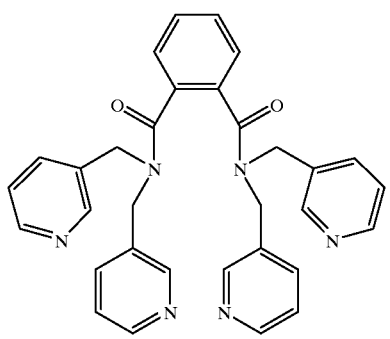

10-10
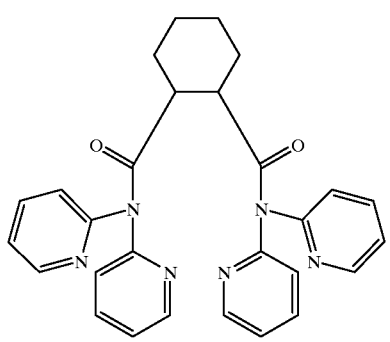

10-11
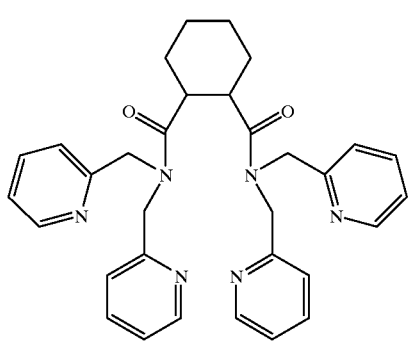

10-12
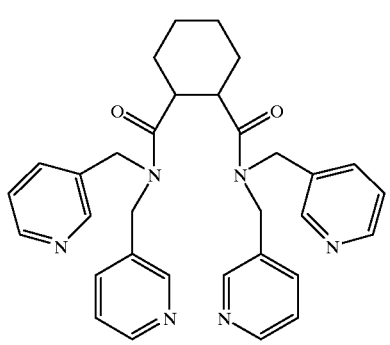

10-13
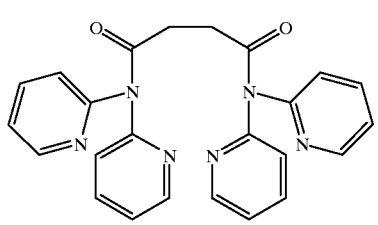

10-14
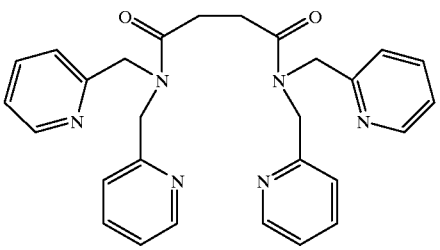

10-15
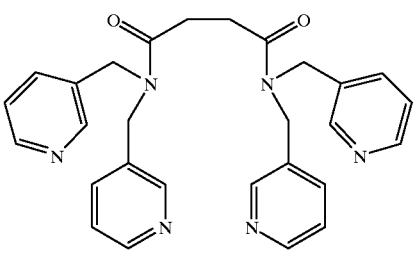

The seventh transition metal complex catalyst used has the formula (VIII):

$$[K^{81}=N-A^8-N=K^{82}] M^{a+}(X^{b-})n \qquad (VIII)$$

wherein $A^8$ is independently an alkylene having 1–6 carbons in the main chain of the group, o-phenylene, m-phenylene, p-phenylene, 1,8-naphthylene, 9,10-phenanthrylene, 2,6-pyridinediyl, 3,6-acrydinediyl, 2,2'-bipyridyl-6,6'-diyl, 1,10-phenanthroline-2,9-diyl, 2,6-pyrimidinediyl, 4,5-pyrimidinediyl, 2,6-pyrazinediyl, 2-phenyl-1,3,5-triazine-2,6-diyl,

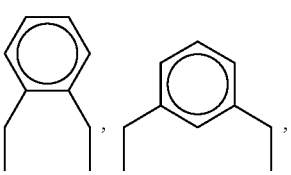

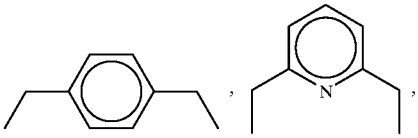

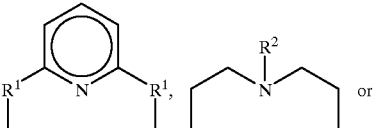 or

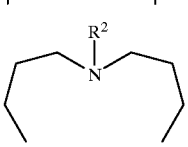

wherein $R^1$ is an alkylene of 1–8 carbons, and R is an alkyl of 1–8 carbons, an aryl of 1–8 carbons, an aryl alkyl of 7–14 carbons or an alkyl aryl of 7–14 carbons, and may carry inactive substituents thereon; $K^{81}$ and $K^{82}$ are a group of the formula:

$$-T-N=CR^{81}-CR^{82}-$$

wherein T is hydroxyl, amino or the general formula:

$$-NR^4R^5$$

wherein $R^4$ and $R^5$ are independently an alkyl of 1–6 carbons and may carry inactive substituents thereon, $R^{81}$ and $R^{82}$ are independently hydrogen, an alkyl of 1–6 carbons or phenyl wherein the alkyl or phenyl may carry inactive substituents thereon; M is a central transition metal ion having a valence of +a; X is a counter ion having a valence of −b which is stable to oxidation; a is an integer of 1–4, b is a positive integer, n is an integer of 1–4, n is equal to a/b, and m is a positive integer of 2 or more.

Preferred examples of the open chain polyfunctional amine compound which forms a ligand in the seventh transition metal complex (VI) are the following compounds 12-01 to 12-26.

12-01
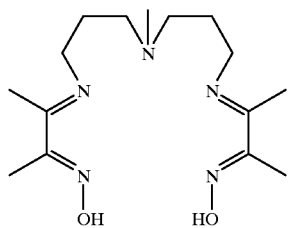

12-02
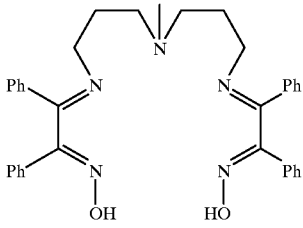

12-03
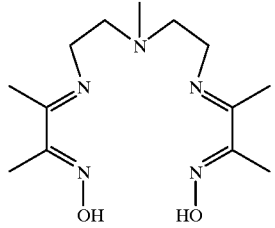

12-04
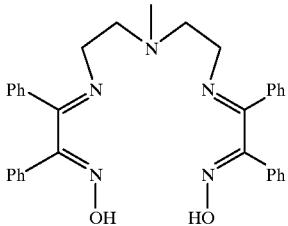

12-05
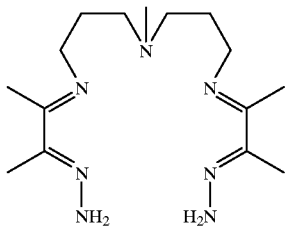

12-06
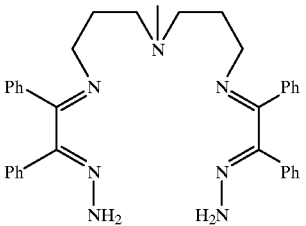

12-07
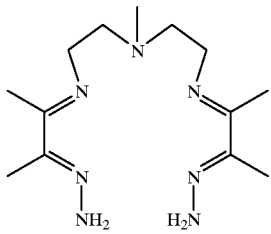

12-08
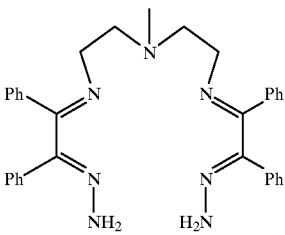

12-09
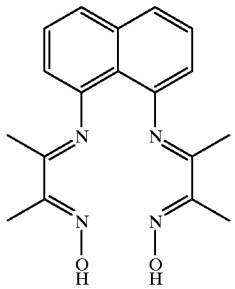

12-10
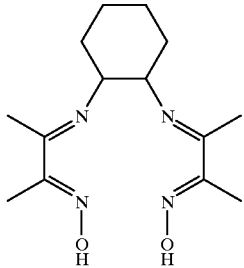

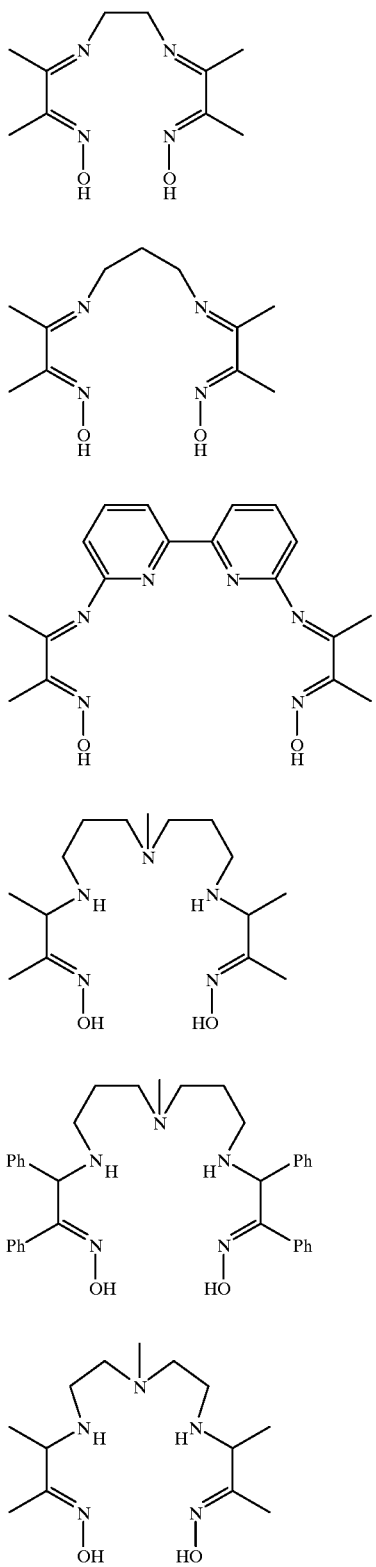
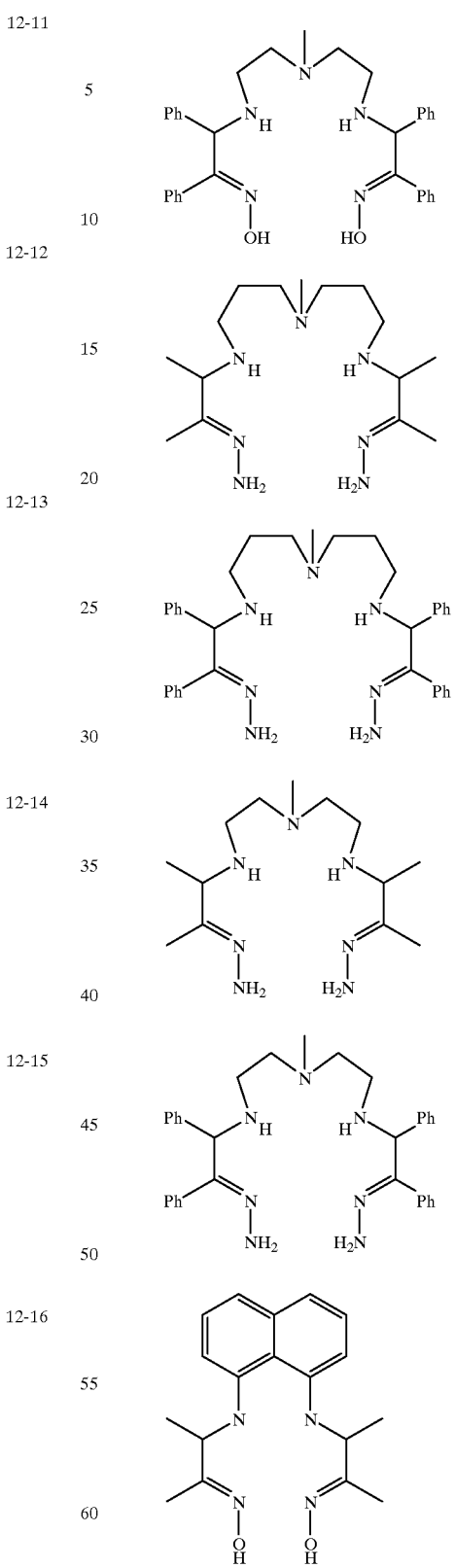

-continued

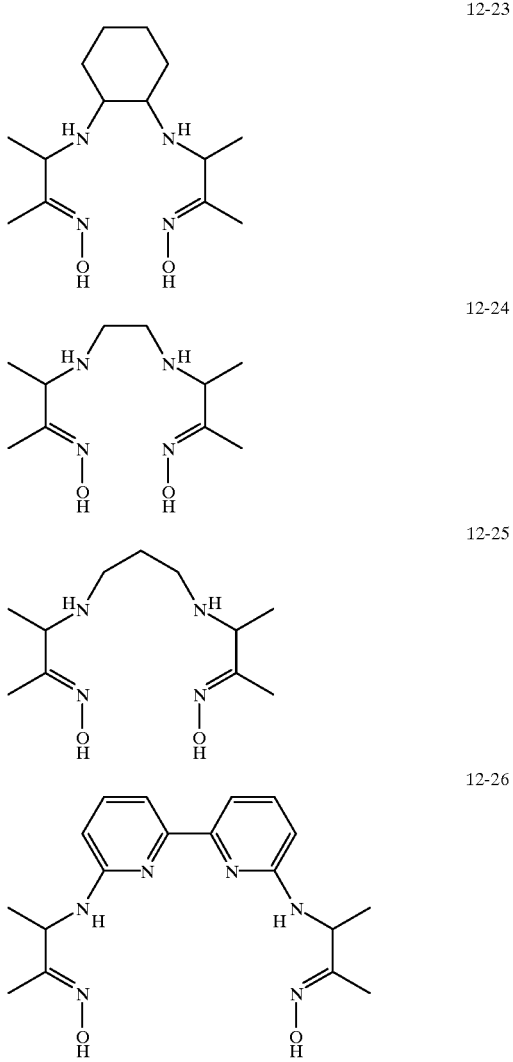

12-23

12-24

12-25

12-26

In any of the formulas of the transition metal complexes which contains, as a ligand, the open chain polyfunctional amine compound as above mentioned, M is a central transition metal ion having a valence of +a wherein a is an integer of 1–4. Preferred examples of the transition metal is iron, nickel, manganese, cobalt, copper, chromium, ruthenium, rhodium, vanadium, titanium or zirconium, among which iron, nickel, manganese, cobalt, copper or ruthenium are particularly preferred.

X is a counter ion having a valence of −b which is stable to oxidation wherein b is a positive integer. Preferred examples of the counter ions are, for example, halide ions such as chloride ion or bromide ion, $SO_4^-$ (sulfate ion), $NO_3^-$, $BF_4^-$, $PF_6^-$, $ClO_4^-$, $CO_3^-$, $P_2O_7^{4-}$, $S_2O_6^{2-}$, organic carboxylic acid anions such as oxalate ion, acetate ion, trifluoroacetate ion, propionate ion, naphthenate ion, benzoate ion, naphthoate ion, organic sulfonic acid anions such as methanesulfonate ion, trifluoromethanesulfonate ion, benzenesulfonate ion or p-toluenesulfonate ion, or peroxide anions such as cumyl peroxide anion. Further examples include acetylacetonate or squarate ion.

In the formulas, a is an integer of 1–4, b is a positive integer, n is an integer of 1–4, n is equal to a/b, and m is a positive integer of 2 or more, preferably 2 or 3.

4. THE REACTION USING THE TRANSITION METAL COMPLEX CATALYSTS

According to the invention, the use of a transition metal complex in the oxidation reaction of aryl alkyl hydrocarbons as a catalyst which contains as a ligand the cyclic or open chain polyfunctional amine compound which has a HOMO energy from −10 eV to −3 eV as calculated by means of MOPAC VERSION 6.0 PM3 METHOD provides the corresonding aryl alkyl hydroperoxides selectively in a high concentration at a high reaction rate without appreciable decomposition of the resulting organic hydroperoxide. As well known, the HOMO energy is an energy which the highest occupied molecular orbital of a molecule has, and the smaller the HOMO energy of a molecule is, the less electron donative the molecule is.

The transition metal complex catalyst used in the invention may be readily prepared by the treatment of an inorganic salt, a carboxylate or a sulfonate of a transition metal with the cyclic or open chain polyfunctional amine compound so that the amine compound is coordinated to the transition metal. More specifically, for example, the treatment of an inorganic salt, a carboxylate or a sulfonate of a transition metal with the amine compound in an appropriate solvent provides the transition metal complex. The resulting transition metal complex may be purified, if necessary, for example, by recrystallization, extraction or chromatographic separation.

The transition metal complex catalyst may be used in the solid state form, or may be dissolved in a reactant or in a reaction solvent. That is to say, the transition metal complex catalyst may be used either in a heterogeneous reaction or in a homogeneous reaction.

The transition metal complex catalyst which contains the cyclic polyfunctional amine compound as a ligand is used in an amount of 0.000001–10 parts by weight, preferably in an amount of 0.00001–1 parts by weight, per 100 parts by weight of the starting aryl alkyl hydrocarbon.

In particular, when the ligand is a cyclic polyfunctional amine compound which has three nitrogen atoms in the ring forming molecular chain, the transition metal complex catalyst is used preferably in an amount of 0.00001–5 parts by weight, more preferably in an amount of 0.0001– 0.1 parts by weight, per 100 parts by weight of the starting aryl alkyl hydrocarbon. In turn, when the ligand is a cyclic polyfunctional amine compound which has four nitrogen atoms or more in the ring forming molecular chain, the catalyst is used preferably in an amount of 0.000001–5 parts by weight, more preferably in an amount of 0.0001–0.1 parts by weight, per 100 parts by weight of the starting aryl alkyl hydrocarbon.

In the meantime, the transition metal complex catalyst which contains the open chain polyfunctional amine compound as a ligand is used preferably in an amount of 0.00001–5 parts by weight, more preferably in an amount of 0.00001–0.1 parts by weight, per 100 parts by weight of the starting aryl alkyl hydrocarbon.

The oxidation of the starting aryl alkyl hydrocarbon is carried out with an oxygen containing gas. Usually air is used as the oxygen containing gas, however, oxygen, carbon dioxide, carbon monoxide, or a mixture of oxygen and nitrogen may be used, if necessary. The reaction is carried out usually under a normal pressure, however, the reaction may be carried out under an increased pressure, if necessary. The reaction temperature may range from about 40° C. to about 130° C., preferably from about 50° C. to about 100° C.

The reaction may be carried out in the presence of a solid alkaline compound or an aqueous solution of an alkaline compound, such as sodium carbonate, sodium bicarbonate, sodium hydroxide, potassium carbonate, potassium hydroxide, potassium hydroxide, barium hydroxide or magnesium oxide. The alkaline compound may be used in an amount of 0.0001–10 parts by weight, preferably in an amount of 0.001–5 parts by weight, per 100 parts by weight of the starting aryl alkyl hydrocarbon.

The reaction may be started with use of a small amount of an initiator, usually the resulting aryl alkyl hydroperoxides, if necessary. For example, cumene monohydroperoxide may be used as an initiator in the oxidation of cumene.

The reaction may be carried out either in a batchwise manner or in a continuous manner. When the reaction is carried out in a batchwise manner, a catalyst is added to the aryl alkyl hydrocarbon if it is liquid at a temperature at which the oxidation reaction is carried out, and air is blown into the mixture under stirring at an elevated temperature. On the other hand, if the starting aryl alkyl hydrocarbon is solid at a temperature at which the oxidation reaction is carried out, the starting hydrocarbon is dissolved in an organic solvent which is inert to the reaction, and then a catalyst is added to the resulting solution, followed by air-blowing into the mixture under stirring at an elevated temperature.

The reaction may be carried out by passing the starting aryl alkyl hydrocarbon or its solution together with air over a fixed catalyst bed.

The resulting aryl alkyl hydroperoxide are readily recovered from the reaction mixture by conventional methods, for example, distillation.

According to the invention, the use of the transition metal complex as a catalyst which contains, as a ligand, a cyclic or an open chain polyfunctional organic amine compound having at least three nitrogen atoms in the molecule in the oxidation of aryl alkyl hydrocarbons with an oxygen containing gas such as air selectively oxidize the starting aryl alkyl hydrocarbons to their corresponding aryl alkyl hydroperoxides in high concentrations at a high reaction rate without appreciable decomposition of the resulting organic hydroperoxides.

5. EXAMPLES

The invention is described in detail with reference to examples. However, the invention is not limited to these examples. In the following, the concentration of cumene monohydroperoxide in the reaction mixture after the reaction was measured by means of iodometry and gas chromatography whereas the selectivity of cumene hydroperoxide was measured by means of gas chromatography.

The results of the reactions in the following examples and comparative examples, namely the concentration of the resulting cumene monohydroperoxide in the reaction mixture after the reaction, the formation rate of cumene monohydroperoxide during the reaction and the selectivity of cumene monohydroperoxide are shown in Tables 1 and 2.

The HOMO energy of cyclic polyfunctional amines used as ligands in the preparation of transition metal complex catalysts are also shown in Tables 1 and 2, which were calculated by use of MOPAC VERSION 6.0 PM3 METHOD.

EXAMPLE I

THE USE OF TRANSITION METAL COMPLEX CATALYSTS CONTAINING CYCLIC POLYFUNCTIONAL AMINES AS LIGANDS

Production of Aryl Alkyl Hydroperoxides by Use of the First Transition Metal Complex Catalysts Wherein the Cyclic Polyfunctional Amine Ligands are Triazacrown Compounds Example 1

20 mg of [1,4,7-triazacyclononane]manganese(II) sulfate was added to a mixture of 90 g of cumene and 10 g of cumene monohydroperoxide. The resulting mixture was heated to 80° C., and the cumene was oxidized for 8 hours with stirring while air was blown into the mixture at a rate of 60 ml per minute.

Example 2

The air oxidation of cumene was carried out in the same manner as in Example 1 for 10 hours by use of 20 mg of N,N',N"-tris(3-hydroxypropyl)-1,4,7-triazacyclononane) manganese(II) sulfate in place of [1,4,7-triazacyclononane] manganese(II) sulfate.

Example 3

The air oxidation of cumene was carried out in the same manner as in Example 1 for 9 hours by use of 2 mg of N,N',N"-tris(3-hydroxypropyl)-1,4,7-triazacyclononane) manganese(II) sulfate in place of [1,4,7-triazacyclononane] manganese(II) sulfate.

Example 4

The air oxidation of cumene was carried out in the same manner as in Example 2 except that 10 ml of distilled water was added to the mixture at the start of the reaction.

Example 5

The air oxidation of cumene was carried out under a pressure of 6 kg/cm$^2$ of air in an autoclave for 6 hours and otherwise in the same manner as in Example 3.

Example 6

The air oxidation of cumene was carried out for 7 hours in the same manner as in Example 5 by use of 5 mg of the complex catalyst.

Comparative Example 1

10 ml of an aqueous solution containing 20 mg of manganese sulfate was added to a mixture of 90 g of cumene and 10 g of cumene monohydroperoxide. The resultant mixture was heated to 80° C., and the cumene was oxidized for 6 hours with stirring while air was blown into the mixture at a rate of 60 ml per minute.

Production of Aryl Alkyl Hydroperoxides by Use of the First Transition Metal Complex Catalyst Wherein the Cyclic Polyfunctional Amine Ligands are Amines Having Four or More Nitrogen Atoms in the Molecule Example 7

10 mg of [1,4,8,11-tetraazacyclotetradecane]manganese (II) sulfate was added to a mixture of 90 g of cumene and 10 g of cumene monohydroperoxide. The resulting mixture was heated to 80° C., and the cumene was oxidized for 8 hours with stirring while air was blown into the mixture at a rate of 60 ml per minute.

Example 8

The reaction was carried out by use of 20 mg of [1,4,8,11-tetraazacyclotetradecane]cobalt(III) chloride in place of [1,4,8,11-tetraazacyclotetradecane]manganese(II) sulfate, and otherwise in the same manner as in Example 7.

Example 9

The reaction was carried out by use of 20 mg of [1,4,8,11-tetraazacyclotetradecane]copper(II) sulfate in place of [1,4,8,11-tetraazacyclotetradecane]manganese(II) sulfate, and otherwise in the same manner as in Example 7.

Example 10

The reaction was carried out by use of 2 mg of [1,4,8,11-tetraazacyclotetradecane]ruthenium(II) sulfate in place of [1,4,8,11-tetraazacyclotetradecane]manganese(II) sulfate, and otherwise in the same manner as in Example 7.

Example 11

The reaction was carried out by use of 20 mg of [1,4,8,11-tetraazacyclotetradecane]nickel(II) sulfate in place of [1,4,8,11-tetraazacyclotetradecane]manganese(II) sulfate, and otherwise in the same manner as in Example 7.

Example 12

The reaction was carried out by use of 2 mg of [1,4,8,11-tetraazacyclotetradecane]manganese(II) benzoate in place of [1,4,8,11-tetraazacyclotetradecane]manganese(II) sulfate, and otherwise in the same manner as in Example 7.

Example 13

The reaction was carried out by use of 2 mg of [1,4,8,11-tetraazacyclotetradecane]cobalt(II) benzoate in place of [1,4,8,11-tetraazacyclotetradecane]manganese(II) sulfate, and otherwise in the same manner as in Example 7.

Example 14

The reaction was carried out by use of 20 mg of [1,4,8,12-tetraazacyclopentadecane]manganese(II) sulfate in place of [1,4,8,11-tetraazacyclotetradecane]manganese(II) sulfate, and otherwise in the same manner as in Example 7.

Example 15

The reaction was carried out by use of 20 mg of [1,4,7,10,13,16-hexaazacyclooctadecane]manganese(II) sulfate in place of [1,4,8,11-tetraazacyclotetradecane]manganese(II) sulfate, and otherwise in the same manner as in Example 7.

Example 16

The reaction was carried out by use of 20 mg of [N,N',N'',N'''-tetrakis(2-ethoxycarbonylethyl)-1,4,8,11-tetraazacyclotetradecane]cobalt(II) sulfate in place of [1,4,8,11-tetraazacyclotetradecane]manganese(II) sulfate, and otherwise in the same manner as in Example 7.

Example 17

The reaction was carried out by use of 2 mg of [1,4,8,11-tetraazacyclotetradecane]manganese(II) stearate in place of [1,4,8,11-tetraazacyclotetradecane]manganese(II) sulfate, and otherwise in the same manner as in Example 7.

Example 18

The reaction was carried out by use of 2 mg of [1,4,8,11-tetraazacyclotetradecane]cobalt(II) stearate in place of [1,4,8,11-tetraazacyclotetradecane]manganese(II) sulfate, and otherwise in the same manner as in Example 7.

Example 19

The reaction was carried out by use of 2 mg of [N,N',N'',N'''-tetra-n-butyl-1,4,8,11-tetraazacyclotetradecane]manganese(II) sulfate in place of [1,4,8,11-tetraazacyclotetradecane]manganese(II) sulfate, and otherwise in the same manner as in Example 7.

Use of the Fifth Transition Metal Complex Catalyst

Example 20

The reaction was carried out in the presence of 2 mg of a transition metal complex obtained by use of cobalt(III) bromide and the compound (6-02) in place of [1,4,8,11-tetraazacyclotetradecane]manganese(II) sulfate, and otherwise in the same manner as in Example 7.

Use of the Third Transition Metal Complex Catalyst

Example 21

To a mixture of 80 g of cumene, 20 g of cumene monohydroperoxide and 50 g of a 0.02% by weight aqueous solution of sodium carbonate, 2 mg of a transition metal complex obtained by use of cobalt sulfate heptahydrate and the compound (4-02). The resulting mixture was heated to 90° C., and the cumene was oxidized for 4 hours with stirring while air was blown into the mixture at a rate of 180 ml per minute.

Use of the Fourth Transition Metal Complex Catalyst

Example 22

The reaction was carried out in the presence of 2 mg of a transition metal complex obtained by use of copper(II) sulfate pentahydrate and the compound (5-02 wherein R bonded to nitrogen is hydrogen and R bonded to carbon is methyl) in place of the complex obtained by use of cobalt sulfate heptahydrate and the compound (4-02), and otherwise in the same manner as in Example 21.

Use of the Second Transition Metal Complex Catalyst

Example 23

The reaction was carried out in the presence of 2 mg of a transition metal complex obtained by use of copper(II) sulfate pentahydrate and the compound (3-01) in place of the complex obtained by use of cobalt sulfate heptahydrate and the compound (4-02), and otherwise in the same manner as in Example 21.

Use of the Fifth Transition Metal Complex Catalyst

Example 24

The reaction was carried out in the presence of 2 mg of a transition metal complex obtained by use of copper(II) sulfate pentahydrate and the compound (6-03) in place of the complex obtained by use of cobalt sulfate heptahydrate and the compound (4-02), and otherwise in the same manner as in Example 21.

Comparative Example 2

The reaction was carried out by use of 2 mg of cobalt(II) (phthalocyanine) in place of [1,4,8,11- tetraazacyclotetradecane]manganese(II) sulfate, and otherwise in the same manner as in Example 7.

Comparative Example 3

The air oxidation of cumene was carried out in the same manner as in Example 7 for 10 hours by use of 2 mg of cobalt(II)(tetraphenylporphyrin) in place of [1,4,8,11-tetraazacyclotetradecane]manganese(II) sulfate.

80° C., and the cumene was oxidized for 8 hours with stirring while air was blown into the mixture at a rate of 60 ml per minute.

After the reaction, the concentration of the resulting cumene monohydroperoxide was found to be 15.8% by weight. Accordingly, the accumulation rate of cumene monohydroperoxide was found to be only 0.72% by weight per hour.

TABLE 1

|  | Reaction Time (hr) | Concentration of CHP (wt %) | Formation Rate of CHP (wt %/hr) | Seletivity of CHP Formation (mol %) | HOMO Energy of Ligand (eV) |
|---|---|---|---|---|---|
| Example 1 | 8 | 21.4 | 1.4 | 87.2 | −8.78 |
| 2 | 10 | 33.6 | 2.3 | 72.9 | −8.84 |
| 3 | 9 | 23.2 | 1.4 | 87.3 | −8.84 |
| 4 | 8 | 16.7 | 0.8 | 84.1 | −8.84 |
| 5 | 6 | 25.1 | 2.5 | 82.0 | −8.84 |
| 6 | 7 | 29.4 | 2.8 | 70.0 | −8.84 |
| Comparative 1 | 6 | 12.2 | 0.34 | 84.0 | — |
| Example 7 | 8 | 30.6 | 2.56 | 80 | −9.00 |
| 8 | 8 | 31.6 | 2.70 | 76 | −9.00 |
| 9 | 8 | 27.6 | 2.20 | 83 | −9.00 |
| 10 | 8 | 27.6 | 2.20 | 77 | −9.00 |
| 11 | 8 | 25.2 | 1.90 | 60 | −9.00 |
| 12 | 8 | 26.0 | 2.00 | 82 | −9.00 |
| 13 | 8 | 25.8 | 1.97 | 75 | −9.00 |
| Example 14 | 8 | 33.0 | 2.87 | 74 | −8.99 |
| 15 | 8 | 32.2 | 2.77 | 71 | −8.97 |
| 16 | 8 | 24.0 | 1.75 | 84 | −9.30 |
| 17 | 8 | 25.9 | 1.99 | 84 | −9.00 |
| 18 | 8 | 26.8 | 2.10 | 83 | −9.00 |
| 19 | 8 | 21.5 | 1.44 | 87 | −8.75 |
| 20 | 8 | 30.2 | 2.52 | 82 | −8.15 |
| 21 | 4 | 28.6 | 2.16 | 90 | −8.27 |
| 22 | 4 | 29.6 | 2.40 | 91 | −8.38 |
| 23 | 4 | 29.7 | 2.42 | 89 | −8.63 |
| 24 | 4 | 29.4 | 2.36 | 90 | −8.71 |
| Comparative 2 | 8 | 30.0 | 2.5 | 58 | −0.40 |
| 3 | 10 | 17.0 | 0.7 | 51 | −0.59 |

CHP: Cumene monohydroperoxide

EXAMPLE II

THE USE OF TRANSITION METAL COMPLEX CATALYSTS CONTAINING OPEN CHAIN POLYFUNCTIONAL AMINES AS LIGANDS

Use of the First Transition Metal Complex Catalysts

Example 1

20 mg of [N,N'-bis(2-aminoethyl)-1,3-propanediamine]manganese (II) sulfate was added to a mixture of 90 g of cumene and 10 g of cumene monohydroperoxide. The resulting mixture was heated to 80° C., and the cumene was oxidized for 8 hours with stirring while air was blown into the mixture at a rate of 60 ml per minute.

After the reaction, the concentration of the resulting cumene monohydroperoxide was found to be 29.6% by weight. Accordingly, the accumulation rate of cumene monohydroperoxide was found to be 2.42% by weight per hour. The selectivity of cumene monohydroperoxide was found to be 77% in spite of the fact that the cumene monohydroperoxide was accumulated in the reaction mixture in an amount of 29.6% by weight.

Comparative Example 1

20 mg of manganese (II) sulfate pentahydrate was added to a mixture of 90 g of cumene and 10 g of cumene monohydroperoxide. The resulting mixture was heated to 80° C., and the cumene was oxidized for 8 hours with stirring while air was blown into the mixture at a rate of 60 ml per minute.

After the reaction, the concentration of the resulting cumene monohydroperoxide was found to be 17.3% by weight. Accordingly, the accumulation rate of cumene monohydroperoxide was found to be only 0.91% by weight per hour.

Comparative Example 2

20 mg of (ethylenediamine)cobalt (II) sulfate was added to a mixture of 90 g of cumene and 10 g of cumene monohydroperoxide. The resulting mixture was heated to 80° C., and the cumene was oxidized for 8 hours with stirring while air was blown into the mixture at a rate of 60 ml per minute.

Use of the First Transition Metal Complex Catalysts

Example 2

The reaction was carried out by use of 20 mg of (tetraethylenepentamine)manganese(II) sulfate in place of [N,N'-bis(2-aminoethyl)-1,3-propanediamine]manganese (II) sulfate, and otherwise in the same manner as in Example 1.

The accumulation rate of cumene monohydroperoxide was found to be 1.96% by weight per hour, and the selectivity of cumene monohydroperoxide was found to be 75%.

Example 3

The reaction was carried out by use of 20 mg of (pentaethylenehexamine)manganese(II) sulfate in place of

69

[N,N'-bis(2-aminoethyl)-1,3-propanediamine]manganese (II) sulfate, and otherwise in the same manner as in Example 1.

The accumulation rate of cumene monohydroperoxide was found to be 1.81% by weight per hour, and the selectivity of cumene monohydroperoxide was found to be 73%.

Example 4

The reaction was carried out by use of 20 mg of (diethylenetriamine)manganese (II) sulfate in place of [N,N'-bis(2-aminoethyl)-1,3-propanediamine]manganese (II) sulfate, and otherwise in the same manner as in Example 1.

The accumulation rate of cumene monohydroperoxide was found to be 1.64% by weight per hour, and the selectivity of cumene monohydroperoxide was found to be 81%.

Example 5

The reaction was carried out by use of 20 mg of [N,N'-bis(2-amino-ethyl)-1,3-propanediamine]cobalt (II) sulfate in place of [N,N'-bis(2-aminoethyl)-1,3-propanediamine] manganese (II) sulfate, and otherwise in the same manner as in Example 1.

The accumulation rate of cumene monohydroperoxide was found to be 2.19% by weight per hour, and the selectivity of cumene monohydroperoxide was found to be 79%.

Example 6

The reaction was carried out by use of 20 mg of [N,N'-bis(2-aminoethyl)-1,3-propanediamine]copper(II) sulfate in place of [N,N'-bis(2-aminoethyl)-1,3-propanediamine] manganese(II) sulfate, and otherwise in the same manner as in Example 1.

The accumulation rate of cumene monohydroperoxide was found to be 1.86% by weight per hour, and the selectivity of cumene monohydroperoxide was found to be 82%.

Example 7

The reaction was carried out by use of 20 mg of [N,N'-bis(2-aminoethyl)-1,3-propanediamine]iron(II) sulfate in place of [N,N'-bis(2-aminoethyl)-1,3-propanediamine] manganese(II) sulfate, and otherwise in the same manner as in Example 1.

The accumulation rate of cumene monohydroperoxide was found to be 1.79% by weight per hour, and the selectivity of cumene monohydroperoxide was found to be 72%.

Example 8

The reaction was carried out by use of 20 mg of [N,N'-bis(2-aminoethyl)-1,3-propanediamine]nickel(II) sulfate in place of [N,N'-bis(2-aminoethyl)-1,3-propanediamine] manganese(II) sulfate, and otherwise in the same manner as in Example 1.

The accumulation rate of cumene monohydroperoxide was found to be 1.80% by weight per hour, and the selectivity of cumene monohydroperoxide was found to be 71%.

Example 9

To a mixture of 90 g of cumene and 10 g of cumene monohydroperoxide, 2 mg of a transition metal complex obtained by treatment of the compound (11-20) with cobalt sulfate was added, and then 50 g of a 0.02% by weight aqueous solution of sodium carbonate was added to the mixture.

The resulting mixture was heated to 90° C., and the cumene was oxidized for 8 hours with stirring while air was blown into the mixture at a rate of 180 ml per minute. The results are shown in Table 2.

In the following, Example 10 uses the first transition metal complex catalyst; Examples 11 to 16 use the third transition metal complex catalyst; Examples 17 and 18 use the fourth transition metal complex catalyst; Examples 19 to 23 use the fifth transition metal complex catalyst; and Examples 24 to 27 use the sixth transition metal complex catalyst.

Examples 10–27

The air oxidation of cumene was carried out in the same manner as in Example 9 by use of 100 g of a mixture of cumene and cumene monohydroperoxide having varied ratios of cumene monohydroperoxide to cumene in the mixture, in the presence of a catalyst in an amount at a temperature for a period of time as shown in Table 2.

Comparative Example 3

The reaction was carried out by use of 2 mg of cobalt(II) (phthalocyanine) in place of (ethylenediamine)cobalt(II) sulfate, and otherwise in the same manner as in Comparative Example 2. The results are shown in Table 2.

Comparative Example 4

The reaction was carried out by use of 2 mg of cobalt(II) (tetraphenylporphyrin) in place of (ethylenediamine)cobalt (II) sulfate, and otherwise in the same manner as in Comparative Example 2. The results are shown in Table 2.

TABLE 2

| | | Metal/ Counter Ion | Catalyst (mg) | Reaction Temperature (° C.) | Initial Concentration of CHP[1] (wt %) | Reaction Time (hr) | Accumulation Rate of CHP[1] (wt %/hr) | Selectivity of CHP[1] Formation mol % | HOMO Energy of Ligand (eV) |
|---|---|---|---|---|---|---|---|---|---|
| | Ligand | | | | | | | | |
| Example 1 | 5-08 | Mn/SO$_4^-$ | 20 | 80 | 10 | 8 | 2.4 | 77 | −9.44 |
| 2 | 5-03 | Mn/SO$_4^-$ | 20 | 80 | 10 | 8 | 2.0 | 75 | −9.43 |
| 3 | 5-04 | Mn/SO$_4^-$ | 20 | 80 | 10 | 8 | 1.8 | 73 | −9.41 |
| 4 | 5-01 | Mn/SO$_4^-$ | 20 | 80 | 10 | 8 | 1.6 | 81 | −9.47 |
| 5 | 5-08 | Co/SO$_4^-$ | 20 | 80 | 10 | 8 | 2.2 | 79 | |
| 6 | 5-08 | Cu/SO$_4^-$ | 20 | 80 | 10 | 8 | 1.9 | 82 | |
| 7 | 5-08 | Fe/SO$_4^-$ | 20 | 80 | 10 | 8 | 1.8 | 72 | |
| 8 | 5-08 | Ni/SO$_4^-$ | 20 | 80 | 10 | 8 | 1.8 | 71 | |
| 9 | 11-20 | Co/SO$_4^-$ | 2 | 90 | 10 | 8 | 1.9 | 91 | −8.89 |
| 10 | 11-05 | Cu/SO$_4^-$ | 2 | 80 | 20 | 5 | 1.7 | 82 | −8.54 |
| 11 | 7-07 | Co/SO$_4^-$ | 10 | 90 | 10 | 3 | 3.7 | 85 | −9.24 |
| 12 | 7-07 | Cu/SO$_4^-$ | 8 | 90 | 20 | 2 | 3.1 | 86 | |
| 13 | 7-08 | Co/SO$_4^-$ | 5 | 90 | 20 | 5 | 2.5 | 85 | −9.25 |
| 14 | 7-08 | Cu/SO$_4^-$ | 8 | 90 | 20 | 3 | 3.1 | 83 | |
| 15 | 7-11 | Co/SO$_4^-$ | 5 | 90 | 10 | 3 | 2.3 | 89 | −8.85 |
| 16 | 7-11 | Cu/SO$_4^-$ | 2 | 80 | 20 | 2 | 1.4 | 85 | |
| Example 17 | 8-01 | Co/SO$_4^-$ | 8 | 90 | 20 | 2 | 3.2 | 88 | −9.31 |
| 18 | 8-01 | Cu/SO$_4^-$ | 5 | 90 | 20 | 5 | 1.8 | 91 | |
| 19 | 9-08 | Co/SO$_4^-$ | 2 | 90 | 10 | 4 | 1.9 | 89 | −9.12 |
| 20 | 9-08 | Cu/SO$_4^-$ | 2 | 90 | 10 | 3 | 3.6 | 84 | |
| 21 | 9-05 | Cu/SO$_4^-$ | 2 | 90 | 20 | 3 | 2.8 | 85 | −9.39 |
| 22 | 9-06 | Cu/SO$_4^-$ | 2 | 80 | 20 | 3 | 2.7 | 69 | −9.03 |
| 23 | 9-07 | Cu/SO$_4^-$ | 2 | 80 | 20 | 3 | 2.8 | 80 | −8.89 |
| 24 | 10-01 | Co/SO$_4^-$ | 2 | 80 | 20 | 4 | 1.7 | 90 | −8.97 |
| 25 | 10-01 | Cu/SO$_4^-$ | 2 | 80 | 20 | 4 | 1.7 | 90 | |
| 26 | 12-01 | Co/SO$_4^-$ | 2 | 80 | 20 | 2 | 2.5 | 87 | −8.88 |
| 27 | 12-01 | Cu/SO$_4^-$ | 2 | 80 | 20 | 2 | 2.0 | 88 | |
| Comparative 1 | — | Mn/SO$_4^-$ | 20 | 80 | 10 | 8 | 0.7 | | |
| 2 | EDA[2] | Mn/SO$_4^-$ | 20 | 80 | 10 | 8 | 0.9 | | −9.34 |
| Comparative 3 | Co(PC)[3] | | 2 | 80 | 10 | 8 | 2.5 | 58 | −0.40 |
| 4 | Co(TPP)[4] | | 2 | 80 | 10 | 10 | 0.7 | 51 | −0.59 |

[1]CHP: cumene monohydroperoxide
[2]EDA: ethylenediamine
[3]Co(PC): cobalt(II) phthalocyanine
[4]Co(TPP): cobalt(II) tetraphenylporphyrin

What is claimed is:

1. A method for producing aryl alkyl hydroperoxides which comprises selectively oxidizing an aryl alkyl hydrocarbon having the formula (I):

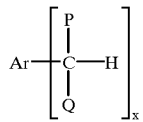
(I)

wherein P and Q are hydrogen or an alkyl and may be the same or different from each other; x is an integer of 1–3; and Ar is an aromatic hydrocarbon group having a valence of x, with an oxygen-containing gas in the presence of a transition metal complex containing a bridged macrocyclic polyamine compound as a ligand and having the formula (III):

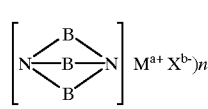
(III)

wherein B is a divalent organic group having the formula (IV):

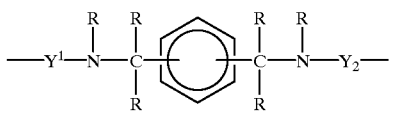

or

wherein $Y^1$ and $Y^2$ are independently an alkylene having 1–6 carbons in the main chain of the group of phenylene, and may carry inactive substituents thereon; R is independently hydrogen, an alkyl, an aryl, an alkyl aryl or an aryl alkyl, and the alkyl, aryl, alkyl aryl or aryl alkyl may carry inactive substituents thereon; M is a central transition metal ion having a valence of +a; X is a counter ion having a valence of −b which is stable to oxidation; a is an integer of 1–4, b is a positive integer, n is an integer of 1–4, n is equal to a/b, and m is 0 or a positive integer of 1 or more.

2. The method as claimed in claim 1, wherein the bridged macrocyclic polyamine compound used in the preparation of the transition metal complex as a ligand has a HOMO energy from −10 eV to −3 eV as calculated by means of MOPAC VERSION 6.0 PM3 METHOD.

3. The method as claimed in claim 1, wherein the transition metal is iron, nickel, manganese, cobalt, copper, chromium, ruthenium, rhodium, vanadium, titanium or zirconium.

4. A transition metal complex which has the formula (III):

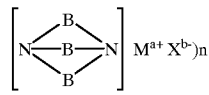
(III)

wherein B is a divalent organic group having the formula (IV):

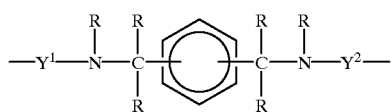
(IV)

or

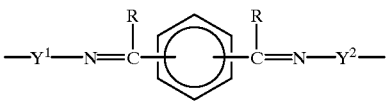
-continued wherein $Y^1$ and $Y^2$ are independently an alkylene having 1–6 carbons in the main chain of the group of phenylene, and may carry inactive substituents thereon; R is independently hydrogen, an alkyl, an aryl, an alkyl aryl or an aryl alkyl, and the alkyl, aryl, alkyl aryl or aryl alkyl may carry inactive substituents thereon; M is a central transition metal ion having a valence of +a; X is a counter ion having a valence of −b which is stable to oxidation; a is an integer of 1–4, b is a positive integer, n is an integer of 1–4, n is equal to a/b, and m is 0 or a positive integer of 1 or more.

* * * * *